United States Patent [19]
Papadopoulou-Rosenzweig et al.

[11] Patent Number: 5,602,142
[45] Date of Patent: Feb. 11, 1997

[54] DNA-AFFINIC HYPOXIA SELECTIVE CYTOTOXINS

[75] Inventors: Maria V. Papadopoulou-Rosenzweig, Skokie; William D. Bloomer, Winnetka, both of Ill.

[73] Assignee: Evanston Hospital Corporation, Evanston, Ill.

[21] Appl. No.: 361,220

[22] Filed: Dec. 21, 1994

[51] Int. Cl.$^6$ .......................... A61K 31/47; C07D 221/06; C07D 219/12
[52] U.S. Cl. .......................... 514/290; 514/292; 514/297; 546/79; 546/82; 546/83; 546/84; 546/88; 546/106
[58] Field of Search .................................... 514/297, 290, 514/292; 546/106, 79, 88, 84, 82, 83

[56] References Cited

U.S. PATENT DOCUMENTS 5,294,715  3/1994  Papadopoulou-Rosenzweig et al.  546/106

FOREIGN PATENT DOCUMENTS 2131020  6/1984  United Kingdom.

OTHER PUBLICATIONS

G. E. Adams et al., "RSU1069, A 2–Nitroimidazole Containing an Alkylating Group: High Efficiency as a Radio–and Chemosensitizer in vitro and in vivo", *Int. J. Radiation Oncology Biol. Phys.*, vol. 10, pp. 1653–1656 (1984).

A. Albert et al., "The Ionisation of Acridine Bases", *J. Chem. Soc.*, pp. 706–713 (1946).

J. M. Brown et al., "SR–2508: A 2–Nitroimidazole Amide Which Should be Superior to Misonidazole as a Radiosensitizer for Clinical Usa", *Int. J. Radiation Oncology Biol. Phys.*, vol. 7, pp. 695–703 (1981).

N. S. Burres et al., "Antitumor Activity and Mechanism of Action of the Novel Marine Natural Products Mycalamide–A and –B and Onnamide", *Cancer Research*, 49, 2935–2940 (Jun. 1, 1989).

D. S. M. Cowan et al., "Targeting Radiosensitizers to DNA by Attachtment of an Intercalating Group: Nitroimidazole–Linked Phenanthridines", *Radiation Research*, 127, pp. 81–89 (1991).

M. F. Dennis et al., "Cellular uptake of misonidazole and analogues with acidic or basic functions", *Int. J. Radiat. Biol.*, vol. 47, No. 6, pp. 629–643 (1985).

W. A. Denny et al., "Interrelations between anti–tumour activity, DNA breakage, and DNA binding kinetics for 9–aminoacridinecarboxamide anti–tumour agents", *Anti–Cancer Drug Design*, 1, pp. 141–147 (1986).

W. A. Denny et al., "NLA–1: A 2–Nitroimidazole Radiosensitizer Targeted to DNA by Intercalation", *Int. J. Radiation Oncology Biol. Phys.*, vol. 22, pp. 553–556 (1992).

W. A. Denny et al., "Hypoxia–Selective Antitumor Agents. 6. 4–(Alkylamino)nitroquinolines: A New Class of Hypoxia–Selective Cytotoxins", *J. Med. Chem.*, 35, pp. 4832–4841 (1992).

J. Feigon et al., "Interactions of Antitumor Drugs with Natural DNA: $^1$H NMR Study of Binding Mode and Kinetics", *J. Med. Chem.*, 27, pp. 450–465 (1984).

T. Fujita et al., "A New Substituent Constant, $\pi$, Derived from Partition Coefficients", *J. Am. Chem. Soc.*, 86, pp. 5175–5180 (1964).

C. Grau et al., "Effect of cancer chemotherapy on the hypoxic fraction of a solid tumor measured using a local tumor control assay", *Radiotherapy and Oncology*, 13, pp. 301–309 (1988).

E. Hatzigrigoriou et al., "2–Alkylsulfonyloxy–3–hydroxy–1,4–naphthoquinones: A Novel Class of Radio–and Chemosensitizers of V79 Cells", *Oncology Research*, vol. 5, No. 1, pp. 29–36 (1993).

K. A. Kennedy, "Hypoxic cells as specific drug targets for chemotherapy", *Anti–Cancer Drug Design*, 2, pp. 181–194 (1987).

A. I. Minchinton et al., "A Comparison of Tumor and Normal Tissue Levels of Acidic Basic and Neutral 2–Nitroimidazole Radiosensitizers in Mice", *Int. J. Radiation Oncology Biol. Phys.*, vol. 12, pp. 1117–1120 (1986).

D. Murray et al., "Enhancement of the DNA cross–linking activity of melphalan by misonidazole in vivo", *Br. J. Cancer*, 47, pp. 195–203 (1983).

R. Panicucci et al., "NLP–1: A DNA Intercalating Hypoxic Cell Radiosensitizer and Cytotoxic", *Int. J. Radiation Oncology Biol. Phys.*, vol. 16, pp. 1039–1043 (1989).

M. V. Papadopoulou et al., "Radiosensitization and Hypoxic Cell Toxicity of NLA–1 and NLA–2, Two New Bioreductive Compounds", *Jpn. J. Cancer Res.*, 83, pp. 410–414 (Apr. 1992).

(List continued on next page.)

*Primary Examiner*—C. Warren Ivy
*Assistant Examiner*—Evelyn Huang
*Attorney, Agent, or Firm*—Marshall, O'Toole, Gerstein, Murray & Borun

[57] ABSTRACT

Hypoxia selective cytotoxins having the structural formula

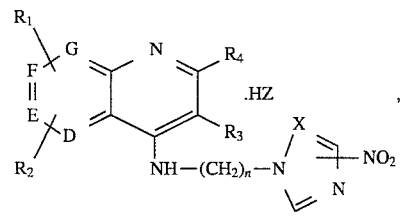

wherein D, E, F and G, independently, are carbon or nitrogen, with the proviso that three or more of D, E, F and G are carbon; $R_1$ and $R_2$, independently, are selected from the group consisting of methyl, halo, hydro, trifluoromethyl, methoxy, cyano, and methylsulfo; $R_3$ and $R_4$, independently, are selected from the group consisting of methyl, ethyl, phenyl, naphthyl, tertiary butyl, halo, halomethylene, hydro, trifluoromethyl, cyano and methylsulfo, or $R_3$ and $R_4$ taken together are a substituted or unsubstituted five or six-membered nonaromatic ring system; n is an integer 1 through 5; X is carbon or nitrogen; and Z is a physiologically acceptable anion, are disclosed. The compounds are useful as radiosensitizers or chemosensitizers, especially in the treatment of cancer patients.

16 Claims, 21 Drawing Sheets

OTHER PUBLICATIONS

M. V. Papadopoulou et al., "Potentiation of 1-(2-Chloroethyl)-3-cyclohexyl-1-nitrosourea's Toxicity in vitro by Two New Bioreductive Agents," *Jpn. J. Cancer Res.*, 83, pp. 907–913 (Aug. 1992).

M. V. Papadopoulou et al., "Nitroheterocyclic–linked acridines as DNA–targeting bioreductive agents", *Drugs of the Future*, 18(3), pp. 231–238 (1993).

M. V. Papadopoulou et al., "Potentiation of Antineoplastic Drugs In Vitro and In Vivo by DNA Intercalating Bioreductive Agents", *Radiation Oncology Investigations*, 1, pp. 206–217 (1993).

K. Reszka et al., "Interaction of the Peroxidase–Derived Metabolite of Mitoxantrone with Nucleic Acids", *Biochemical Pharmacology*, vol. 38, No. 23, pp. 4253–4260 (1989).

M. A. Robbie et al., "Mechanism of Resistance of Noncyclic Mammalian Cells to $4^1$–(9–Acridinylamino)methanesulfon–m–anisidide: Comparison of Uptake, Metabolism, and DNA Breakage in Log–and Plateau–Phase Chinese Hamster Fibroblast Cell Cultures", *Cancer Research*, 48, pp. 310–319 (Jan. 15, 1988).

P. B. Roberts et al., "Radiosensitization of Mammalian Cells in Vitro by Nitroacridines", *Radiation Research*, 123, pp. 153–164 (1990).

D. A. Rowley et al., "DNA Damage by Superoxide–Generating Systems in Relation to the Mechanism of Action of the Anti–Tumour Antibiotic Adriamycin", *Biochimica et Biophysica Acta*, 761, pp. 86–93 (1983).

A. C. Sartorelli, "Therapeutic Attack of Hypoxic Cells of Solid Tumors: Presidential Address", *Cancer Research*, 48, pp. 775–778 (Feb. 15, 1988).

D. Siemann, "Modification of Chemotherapy by Nitroimidazoles", *Int. J. Radiation Oncology Biol. Phys.*, vol. 10, pp. 1585–1594 (1984).

B. G. Siim et al., "Does DNA Targeting Affect the Cytotoxicity and Cell Uptake of Basic Nitroquinoline Bioreductive Drugs?", *Int. J. Radiation Oncology Biol. Phys.*, vol. 29, No. 2, pp. 311–315 (1994).

W. J. Slichenmyer et al., "The Current Status of Camptothecin Analogues as Antitumor Agents", *Journal of the National Cancer Institute*, vol. 85, No. 4, pp. 271–291 (Feb. 17, 1993).

P. J. Smith et al., "Modification of the radiation sensitivity of human tumour cells by a bis–benzimidazole derivative", *Int. J. Radiat. Biol.*, vol. 46, No. 4, pp. 331–344 (1984).

G. G. Steel et al., "Exploitable Mechanisms in Combined Radiotherapy–Chemotherapy: The Concept of Additivity", *Int. J. Radiation Oncology Biol. Phys.*, vol. 5, pp. 85–91 (1979).

M. R. L. Stratford et al., "Radiosensitizer–DNA Interactions in Relation to Intracelluar Uptake", *Int. J. Radiation Oncology Biol. Phys.*, vol. 16, pp. 1007–1010 (1989).

I. Tannock et al., "Response of Chinese Hamster Ovary Cells to Anti–Cancer Drugs Under Aerobic and Hypoxic Conditions", *Br. J. Cancer*, 43, p. 245 (1981).

Y. C. Taylor et al., "Mechanism of Sensitization of Chinese Hamster Ovary Cells to Melphalan by Hypoxic Treatment with Misonidazole", *Cancer Research*, 43, pp. 3175–3181 (Jul. 1983).

W. R. Wilson et al., "Reductive Metabolism and Hypoxia–Selective Toxicity of Nitracrine", *Int. J. Radiation Oncology Biol. Phys.*, vol. 12, pp. 1235–1238 (1986).

W. R. Wilson et al., "5–Nitro–4–(N, N–dimethylaminopropylamino)quinoline(5–Nitraquine), a New DNA–Affinic Hypoxic Cell Radiosensitizer and Bioreductive Agent: Comparison with Nitracine", *Radiation Research*, 131, pp. 257–265 (1992).

M. Yamato et al., "Synthesis and Antitumor Activity of Fused Tetracyclic Quinoline Derivatives", *J. Med. Chem.*, 32, pp. 1295–1300 (1989).

L. Zwelling, "DNA topoisomerase II as a target of antineoplastic drug therapy", *Cancer and Metastatis Reviews* 4, pp. 263–276 (1985).

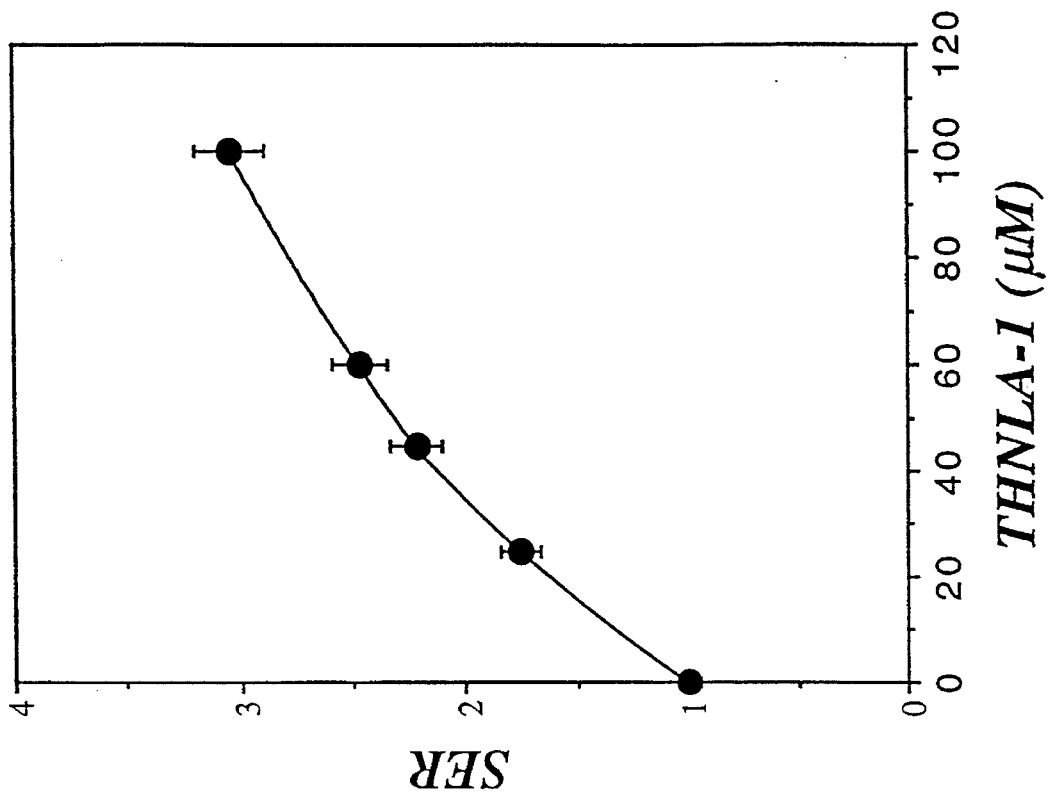
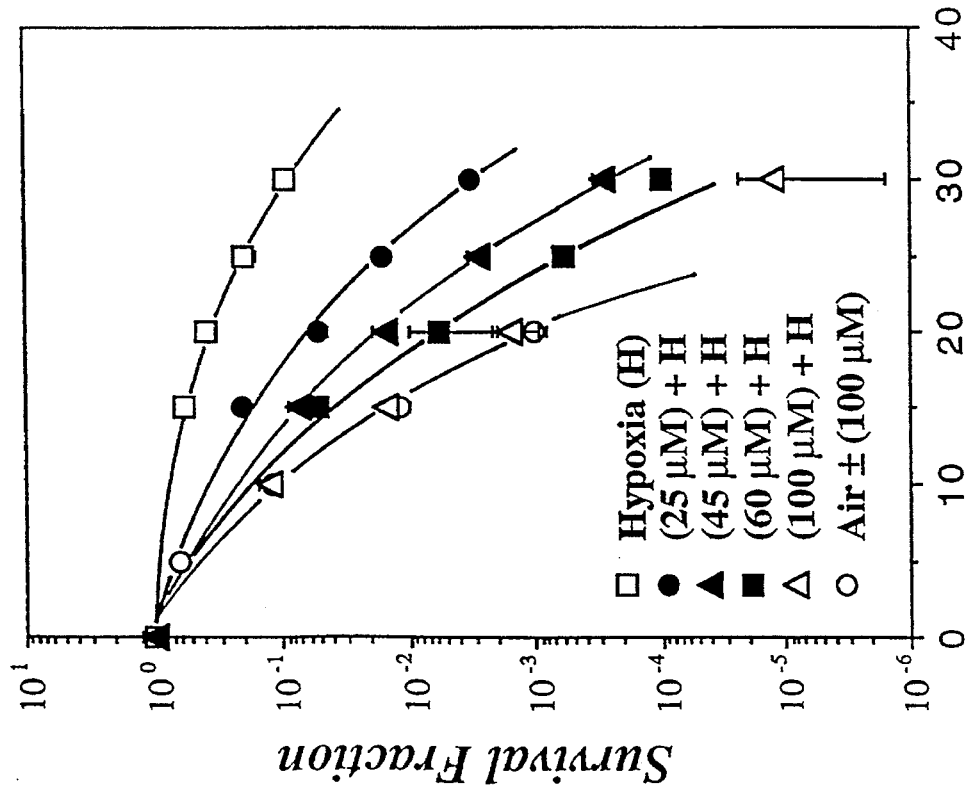
FIGURE 3B
FIGURE 3A

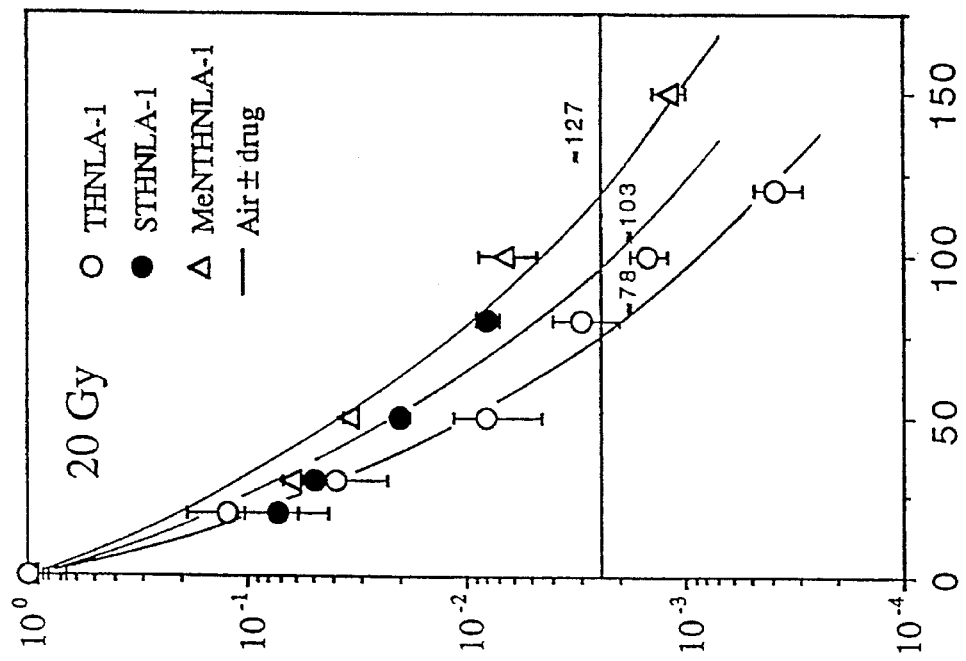
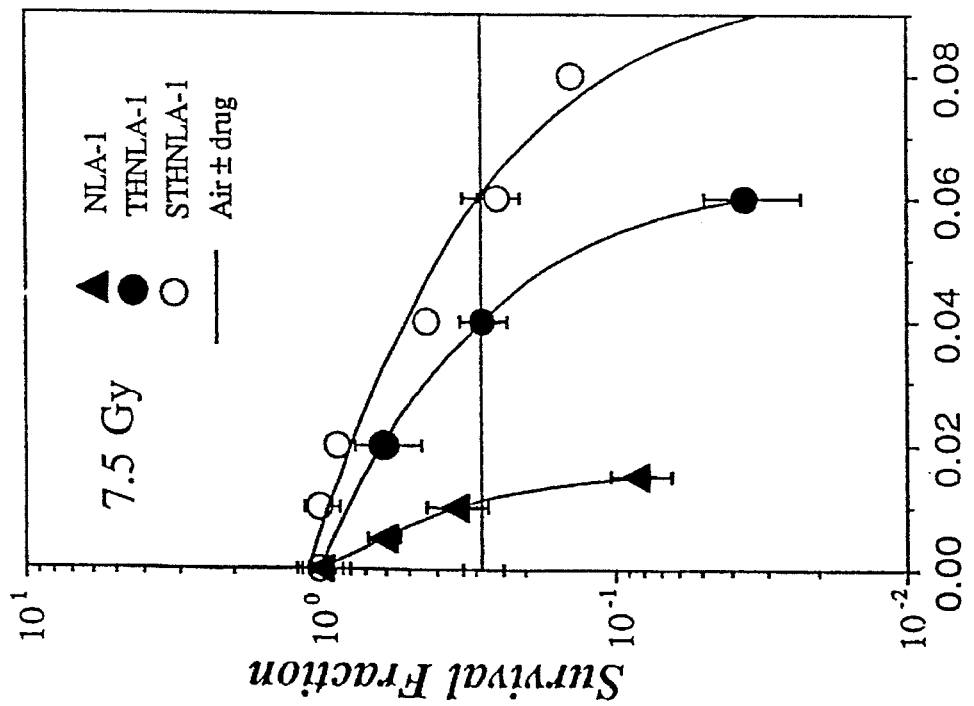
FIGURE 6B
FIGURE 6A

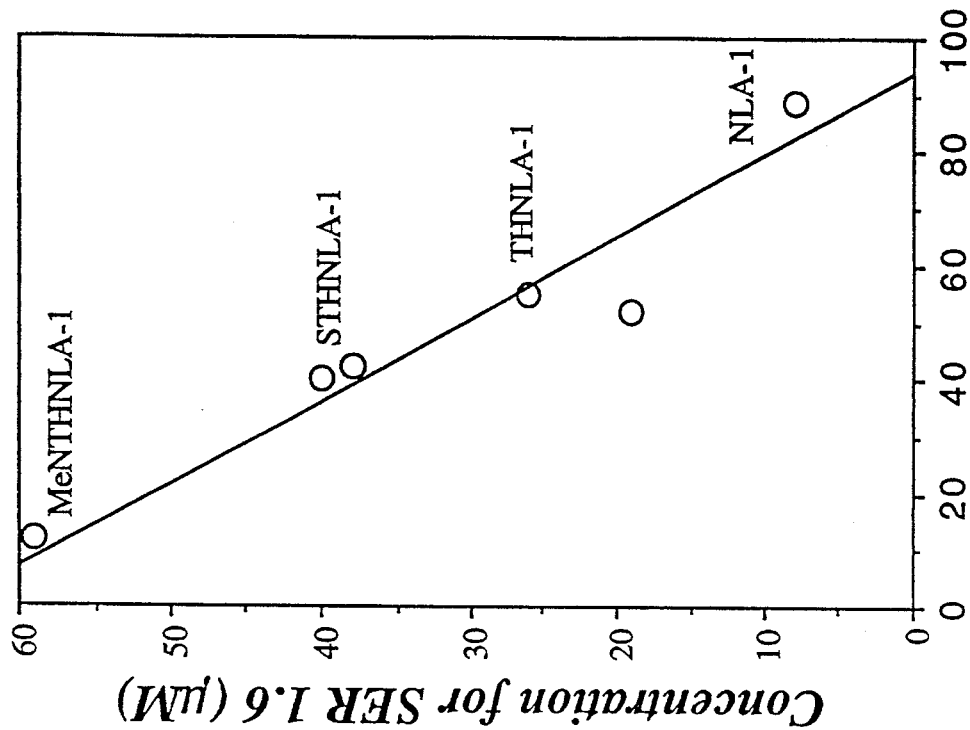
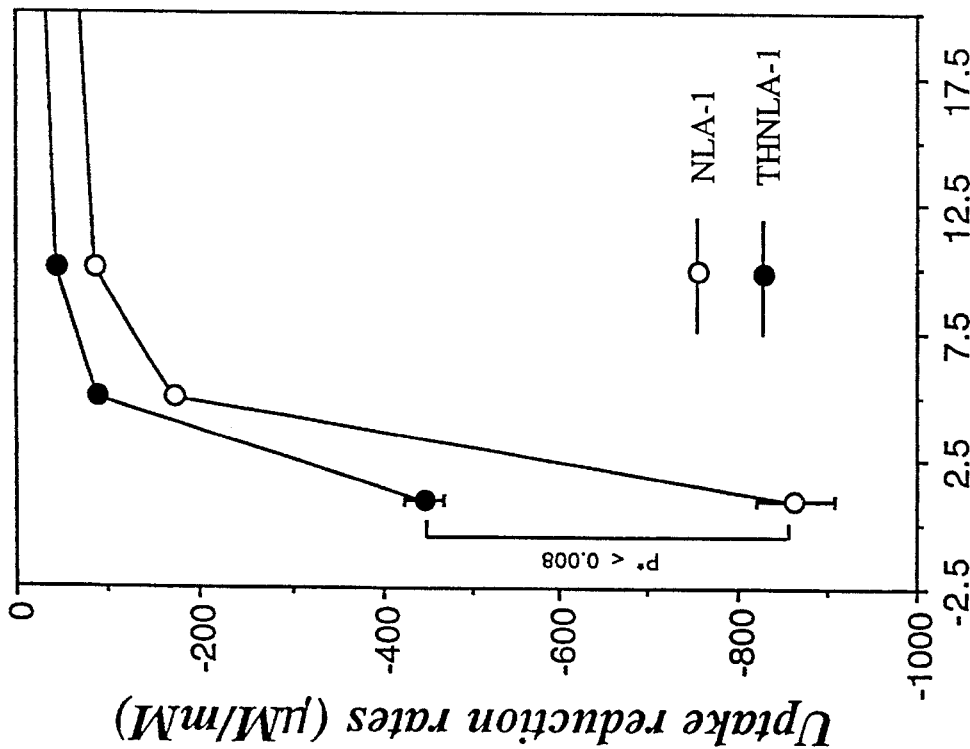
FIGURE 11B
FIGURE 11A

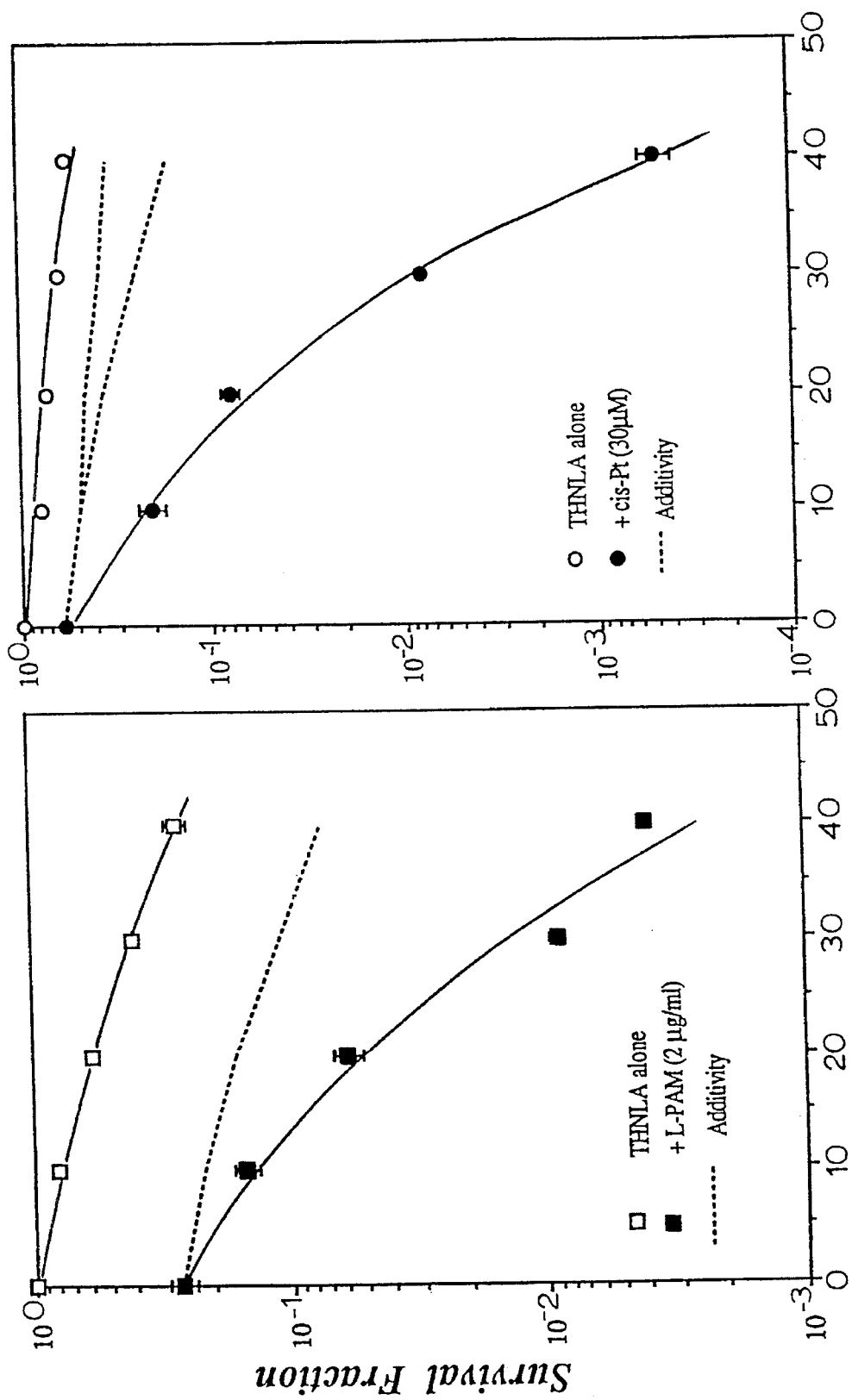
FIGURE 13A THNLA-1 (μM)
FIGURE 13B THNLA-1 (μM)

DNA-AFFINIC HYPOXIA SELECTIVE CYTOTOXINS

FIELD OF THE INVENTION

The present invention generally relates to cancer therapy and to compounds and methods of sensitizing tumor cells to radiation therapy and chemotherapy. More particularly, the present invention relates to a novel class of DNA-affinic hypoxia selective cytotoxins which radiosensitize and chemosensitize hypoxic tumor cells.

BACKGROUND OF THE INVENTION

Malignant tumors often demonstrate a resistance to radiation therapy and chemotherapy. The resistance of physiologically hypoxic regions within solid tumors during cancer treatment is an important reason for the failure of radiotherapy and chemotherapy to eradicate such tumors.

Investigators have made progress in understanding the basic cellular and molecular mechanisms of therapeutic resistance. Many of these investigative efforts have focused on intrinsic cellular characteristics. However, there is an aspect of therapeutic resistance which is related to the physiologic and biochemical state of the cell, and not to intrinsic cellular properties. In other words, cells which are otherwise sensitive to cytotoxin treatment under normal physiologic conditions, are resistant because of their particular physiologic state within the tumor.

For example, it has long been known that hypoxic, i.e., oxygen deficient, cells are relatively resistant to killing by radiation. To achieve the same proportion of cell kill, about three times the radiation dose is required for hypoxic cells compared to the radiation dose required for well-oxygenated cells. Thus oxygen has the ability to sensitize cells to ionizing radiation at clinical radiation doses. Overcoming this resistance of hypoxic cells has been investigated as a means of improving the efficacy of ionizing radiation.

Multiple mechanisms have been proposed to explain hypoxic resistance to radiation therapy and chemotherapy. The proposed mechanisms involve kinetic, metabolic, and physical factors. For example, hypoxic cells frequently are noncycling and therefore are refractory to proliferation-dependent cytotoxic drugs. In addition, the cell can be in a metabolically-compromised state and unable to concentrate and activate potentially-effective agents. The distance between a cell and blood vessels also can be greater than the diffusion distance of many chemotherapeutic agents.

Efforts to overcome hypoxia in clinical cancer treatments have involved the development of hypoxic cell radiosensitizers and chemosensitizers which substitute for, or mimic, oxygen.

Cell kill by ionizing radiation is caused by damage to the DNA. The target radical on the DNA, designated "DNA-", is produced by either direct ionization or reaction with hydroxyl radicals produced radiolysis of neighboring water molecules. Reaction with oxygen produces a peroxyl radical, $DNA-O_2 \cdot$, which forms products leading to irreversible DNA damage. Radiosensitizers are designed to mimic oxygen by reacting with DNA radicals to form covalent adducts at the radical sites.

As discussed hereafter, the ability of oxygen or a sensitizer to enhance cell kill is reflected in the enhancement ratio, i.e., OER for oxygen and SER (sensitizer enhancement ratio) for the sensitizer. The OER is dependent on the concentration of oxygen present at the target at the time of irradiation. Similarly, the oxygen-mimicking effect of a hypoxic cell sensitizer (SER) depends primarily on the concentration of sensitizer at the target at the time of irradiation. However, the oxygen-mimicking sensitizers preferentially affect hypoxic cells, which typically comprise only about 20% of the tumor. Therefore, in estimating the degree of enhancement of cell kill, the SER applies only to hypoxic cells, not to the entire tumor.

It is well established that bioreductive compounds, such as nitroimidazole-based compounds, potentiate the cytotoxic effects of radiation and several chemotherapeutic agents towards hypoxic tumor cells, both in vitro and in vivo. Bioreductive compounds are readily activated by metabolic reduction in a hypoxic environment and enhance the susceptibility of hypoxic tumor cells to radiation and conventional anticancer drugs.

Bioreductive agents typically are compounds of high electron affinity. Bioreductive agents have the ability to kill hypoxic cells directly because of their preferential reductive metabolism under hypoxic conditions, where the limited oxygen concentration cannot significantly antagonize the reduction process. In addition, solid tumors develop physiological hypoxia to a greater degree than normal tissues, and evidence exists that tumor cells have relatively high levels of reductive enzymes.

Bioreductive agents in hypoxic cells therefore mimic the oxygen effect in oxygenated cells during irradiation, and cause fixation of radiation-induced damage to DNA or other vital macromolecules. Thus, bioreductive agents act as radiosensitizers of hypoxic cells. Bioreductive agents can also act as chemosensitizers for conventional anticancer drugs by enhancing the susceptibility of hypoxic tumor cells to chemotherapy.

The combination of a sensitizer with either radiation or a conventional anticancer drug helps overcome the problem of hypoxic cell resistance to cancer therapy. Chemosensitization in vitro usually is demonstrated by pretreating cells with a sensitizer under hypoxic conditions before exposure to the chemotherapeutic drug, often an alkylating agent, under aerobic conditions. This "preincubation effect" is attributed predominantly to a reduction of the sensitizer which occurs under hypoxic conditions.

Investigators have searched for improved hypoxic cell sensitizers that are non-toxic to aerobic and that concentrate more effectively in tumors. One hypoxic cell radiosensitizer is misonidazole (MISO), an electron-affinic 2-nitroimidazole which has shown some benefit in certain situations. However, MISO exhibits significant neurotoxicity and, consequently, the total dose of MISO that can be administered to a patient is limited. Another hypoxic cell sensitizer is etanidazole (SR-2508), a neutral compound which is more hydrophilic than MISO, is less neurotoxic, and can be administered to humans at about a threefold higher dose than MISO.

A third hypoxic cell sensitizer is pimondazole (Ro 03-8799), which contains a basic piperidine moiety and has a total dose limitation similar to MISO. A fourth compound, RSU-1069, is a bifunctional molecule containing a 2-nitroimidazole group and an alkylating aziridine. In experimental systems, RSU-1069 has a substantially greater activity than MISO, and is toxic to hypoxic cells in vitro at about a 100-fold lower concentration compared to the toxic concentration for aerobic cells.

Bioreductive radiosensitizers also have an ability to significantly enhance the activity of several chemotherapeutic agents, such as, e.g., cyclophosphamide, nitrosoureas, L-phenylalanine mustard (i.e., L-PAM or 4-[bis(2-chloroethyl)amino]-L-phenylalanine), cis-diamminedichloroplatinum(II) (i.e., cis-DDP) and doxorubicin, in vitro and in vivo. This enhancement of chemotherapeutic activity is known as chemosensitization or chemopotentiation.

Although significant progress has been made in developing bioreductive drugs as radio- and chemosensitizers, further development is necessary because none of the bioreductive drugs tested to date has shown impressive clinical results. Currently, therefore, there is a strong interest in targeting bioreductive agents to DNA in order to improve the radio- and chemosensitizing properties of such agents. Efforts to increase cytotoxic efficacy have centered on increasing the concentration of sensitizer within DNA as opposed to increasing the average intracellular concentration. Some investigators targeted DNA by combining an alkylating agent with bioreductive functional groups within the same drug (e.g., RSU-1069). Other investigators used transition metal coordination complexes such as platinum and ruthenium to target nitroaromatic radiosensitizers to DNA. However, these metal coordination complexes often are less effective as radiosensitizers than the free radiosensitizer molecule, even though the one electron reduction potential (a property related to sensitization efficiency) can be increased in some platinum complexes compared to the free sensitizer molecule.

Another approach to improve targeting of bioreductive agents to DNA involves using an intercalating moiety such as a phenanthridine or an acridine, which inserts itself between two adjacent sets of base pairs of the DNA. Non-covalent binding to DNA, such as through intercalation, permits migration of the radiosensitizer to DNA sites where radiation induced radicals are created.

For example, NLP-1, 5-[3-(2-nitro-1-imidazolyl)-propyl] phenanthridinium bromide, a 2-nitroimidazole-linked phenanthridine, has been synthesized. The synthesis, hypoxic cell cytotoxicity and radiosensitization of NLP-1 has been reported by R. Panicucci et al., Int. J. Radiat. Oncol. Biol. Phys., 16, pages 1039–1043 (1989), incorporated herein by reference.

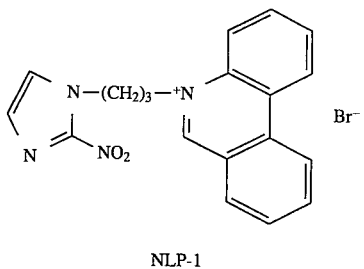

NLP-1

An acridine-based hypoxia selective cytotoxin is preferred over the phenanthridine-based compound because acridine is a better intercalator than phenanthridine. Nitracrine, 1-nitro-acridine, is a potent hypoxia selective cytotoxin and a radiation sensitizer in mammalian cell cultures; however, rapid metabolism limits the radiosensitization efficacy of nitracrine in vivo. See, P. B. Roberts et al., Radiation Research, 123, pages 153–164 (1990), incorporated herein by reference.

An acridine-based hypoxia selective cytotoxin that is relatively stable in vivo therefore is preferred. In addition, it is preferred that the hypoxia selective cytotoxin does not bind tightly to DNA. For example, 1-nitracrine, which exhibits faster dissociation kinetics from DNA than the other nitroacridine isomers, is twenty times more potent as a sensitizer than other nitracrine isomers tested.

Papadopoulou-Rosenzweig et al. U.S. Pat. No. 5,294,715, incorporated herein by reference, discloses hypoxia selective cytotoxins having the structure

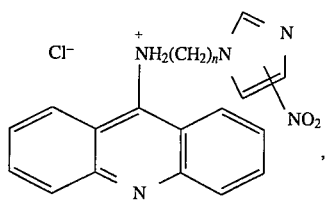

wherein n is from 1 to 5, and $NO_2$ is in at least one of the 2, 4 or 5-positions of the imidazole ring.

The compounds disclosed in Papadopoulou-Rosenzweig et al. U.S. Pat. No. 5,294,715 include an aromatic acridine moiety and are useful as radiosensitizers and chemosensitizers. These acridine-based compounds are electron affinic and exhibit strong DNA intercalating properties. However, the acridine-based compounds demonstrated a less than expected radiosensitization in vivo. This unexpectedly low radiosensitization has been attributed to restricted mobility of the acridine-based compounds along the DNA backbone, and to low extravascular diffusion in tumors. Mobility along the DNA backbone is considered a significant factor with respect to trapping radiation-induced radicals and providing good radiosensitization and chemosensitization efficacy.

Investigators therefore have continued efforts to develop a hypoxia selective cytotoxin and sensitizer having a lower affinity to bind to DNA and having enhanced efficacy. Accordingly, the present invention is directed to bioreductive cytotoxins which enhance the cytotoxic activities of ionizing radiation and chemotherapeutic agents to hypoxic cells, which are inherently cytotoxic to hypoxic cells, and which are essentially nontoxic to aerobic cells.

SUMMARY OF THE INVENTION

The present invention is directed to a novel class of compounds that are DNA affinic and that exhibit substantial mobility along the DNA backbone. The compounds are useful as sensitizers in radiotherapy and chemotherapy. In particular, the present invention is directed to a novel class of compounds which act as hypoxia selective cytotoxins and which do not exhibit significant aerobic toxicity at effective radio- and chemosensitization doses.

Therefore, one aspect of the present invention is to provide bioreductive compounds having radiosensitization and chemosensitization properties. The compounds are capable of binding to DNA by intercalation, and exhibit a significant mobility along the DNA backbone. The compounds also are more selectively toxic to hypoxic cells than to aerobic cells. The novel hypoxia selective compounds are useful in methods of treating cancer by potentiating the toxic effect of radiation and chemotherapy. The present hypoxia selective compounds also exhibit improved radiosensitization and chemosensitization over prior sensitizers.

In particular, the present invention is directed to hypoxia selective cytotoxins having general structural formula (I):

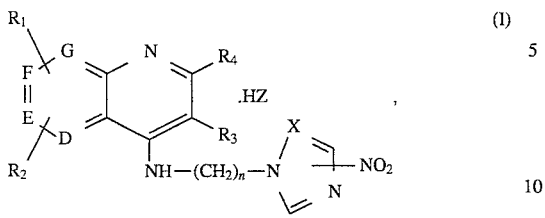

wherein D, E, F and G, independently, are carbon or nitrogen, with the proviso that three or more of D, E, F and G are carbon; $R_1$ and $R_2$, independently, are selected from the group consisting of methyl, halo, hydro (i.e., H), trifluoromethyl, methoxy, cyano, and methylsulfo; $R_3$ and $R_4$, independently, are selected from the group consisting of methyl, ethyl, tertiary butyl, phenyl, naphthyl, halo, halomethylene, hydro, trifluoromethyl, cyano, and methylsulfo, or $R_3$ and $R_4$ taken together are a substituted or unsubstituted five or six-membered nonaromatic ring system; n is an integer 1 through 5; X is carbon or nitrogen; and Z is a physiologically acceptable anion.

In another aspect of the present invention, the preferred hypoxia selective cytotoxins have $R_3$ and $R_4$ groups that are taken together to form a substituted or unsubstituted five or six-membered nonaromatic ring system. Exemplary hypoxia selective cytotoxins of the present invention therefore include, but are not limited to, 9-[3-(2-nitro-1-imidazolyl)propylamino]-1,2,3,4-tetrahydroacridine hydrochloride (THNLA-1), 10-[3-(2-nitroimidazolyl)propylamino]-3,4-dihydro-1-H-thiopyrano[4,3-b]quinoline hydrochloride (S-THNLA-1), 10-[3-(2-nitroimidazolyl) propylamino]-2-methyl-1,2,3,4-tetrahydro-benzo[b]-1,6-naphthyridine hydrochloride (MeN-THNLA-1) and 9-[3-(2-nitro-1-imidazolyl)propylamino]cyclopenten[b]quinoline hydrochloride (NLCPQ-1), having the structural formulae

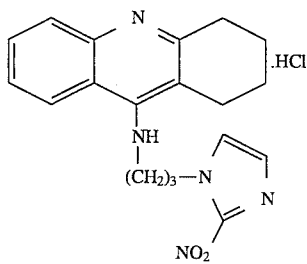

THNLA-1

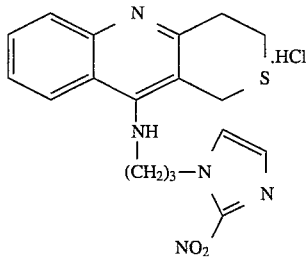

S-THNLA-1

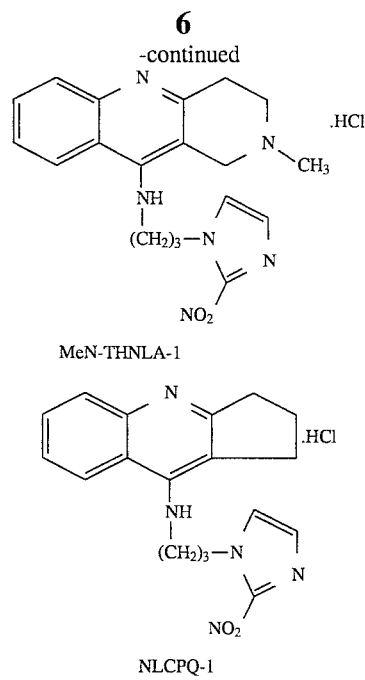

MeN-THNLA-1

NLCPQ-1

In another aspect of the present invention, in addition to the fused aromatic ring system including two rings (e.g., the quinoline ring system), the present hypoxia selective cytotoxins also include a nonplanar, nonaromatic fused ring, or other suitable substituent or substituents, bonded to the b-ring of the aromatic fused ring system to increase the mobility of the hypoxia selective cytotoxin along the DNA backbone by decreasing the binding efficacy to DNA.

Another aspect of the present invention is to provide a method of radiosensitization comprising administering an effective amount of the hypoxia selective cytotoxin of structural formula (I), then administering ionizing radiation.

Another aspect of the present invention is to provide a method of chemosensitization comprising administering an effective amount of a hypoxia selective cytotoxin of general formula (I), then administering a chemotherapeutic agent.

Another aspect of the present invention is to provide a method of radiosensitization comprising administering an effective dose of THNLA-1, S-THNLA-1, MeN-THNLA-1 or NLCPQ-1, then administering ionizing radiation.

Another aspect of the present invention is to provide a method of chemosensitization comprising administering an effective dose of THNLA-1, S-THNLA-1, MeN-THNLA-1 or NLCPQ-1, then administering a chemotherapeutic agent.

Yet another aspect of the present invention is to provide a method of targeting a hypoxia selective cytotoxin to the DNA of hypoxic tumor cells comprising treatment with compounds having general structural formula (I).

The present compounds are particularly well suited as hypoxia selective cytotoxins due to the feature of a nitroimidazole moiety as the hypoxiaselective moiety. In accordance with an important aspect of the present invention, the nitroimidazole moiety is linked to a quinoline-based, fused aromatic ring system through an alkylamino chain. The compounds effectively target the sensitizing moiety to DNA through intercalation. In a preferred form, the present compounds are positively charged to increase sensitizer concentration near the negatively-charged phosphate moieties present in the DNA backbone. The present compounds further feature a nonplanar, nonaromatic ring, or other suitable substituents, bonded to the b-ring of the quinoline ring system. The nonplanar nonaromatic ring, or other substituents, increase the mobility of the hypoxia selective cytotoxin along the DNA backbone due to weaker binding to DNA.

BRIEF DESCRIPTION OF THE DRAWINGS

The above and other aspects and advantages of the present invention will become apparent from the following detailed description of the preferred embodiments illustrated in the accompanying figures wherein:

FIG. 3A is a plot of survival fraction of hypoxic or aerobic V79 cells vs. radiation doses for various THNLA-1 concentrations;

FIG. 3B is a plot of SER (sensitization enhancement ratio) vs. THNLA-1 concentration;

FIGS. 6A and 6B are plots of survival fraction vs. concentration of NLA-1, THNLA-1 and S-THNLA-1 at a radiation dose of 7.5 Gy or 20 Gy under aerobic or hypoxic conditions;

FIG. 11A is a plot of uptake reduction rates for NLA-1 and THNLA-1 (in μM per mM of $NH_4Cl$) vs. ammonium chloride concentration;

FIG. 11B is a plot of hypoxia selective cytotoxin concentration necessary for an SER of 1.6 vs. $C_i/C_e$ for various hypoxia selective cytotoxins;

FIGS. 13A and 13B are plots of survival fraction of V79 cells vs. THNLA-1 concentration (μM), wherein THNLA-1 is present alone or in the presence of L-PAM or cis-DDP, also plotted is the survival fraction expected from a combination of THNLA-1 and either L-PAM or cis-DDP;

DETAILED DESCRIPTION OF THE PREFERRED EMBODIMENTS

Figures 1A, 1B:
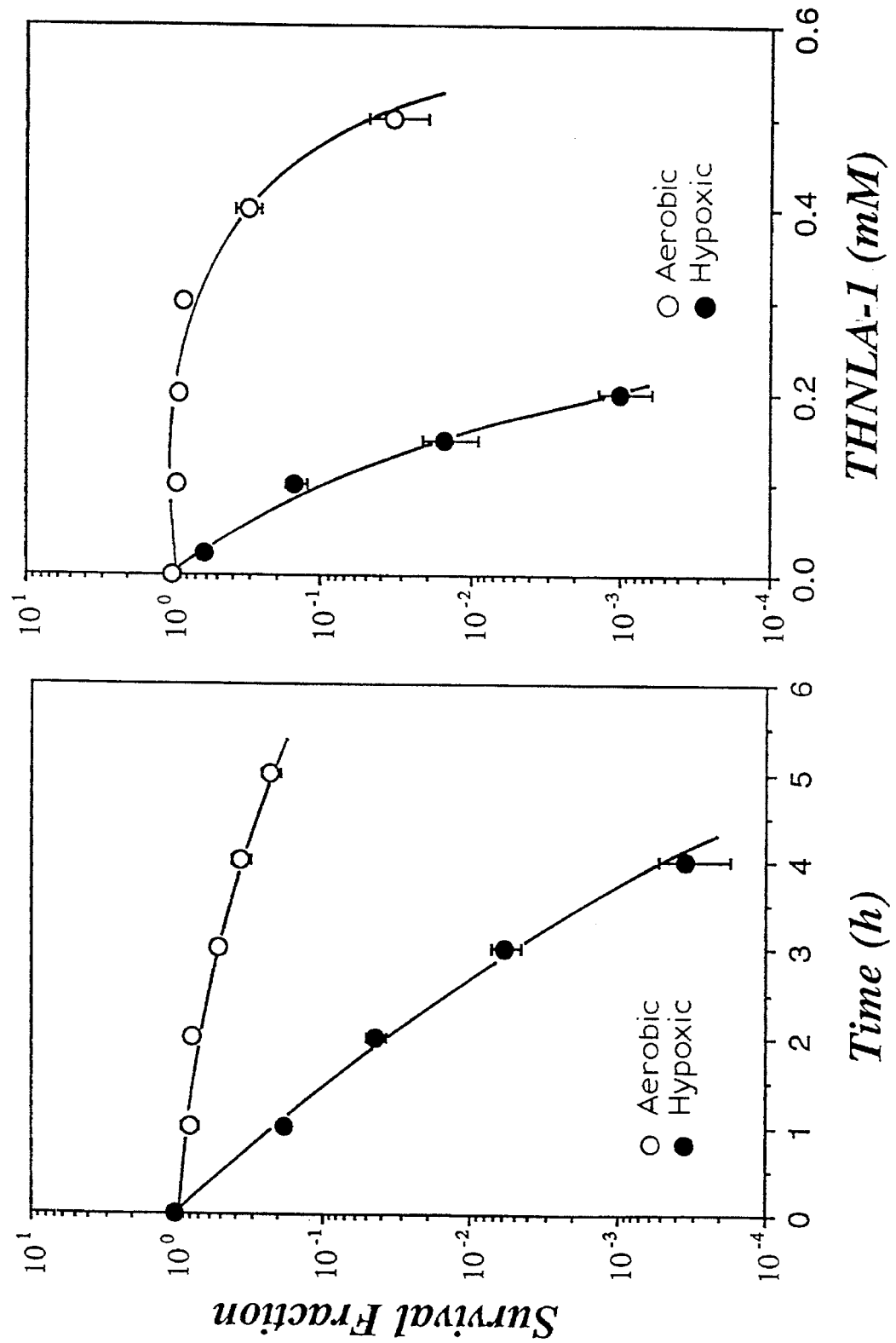
FIG. 1A is a plot of survival fraction of V79 Chinese hamster lung cells vs. time for a constant 0.1 mM (millimolar) concentration of THNLA-1 under aerobic or hypoxic conditions.
FIG. 1B is a plot of survival fraction of V79 cells vs. THNLA-1 concentration after a one hour time period at 37° C. under aerobic or hypoxic conditions.

By directing an electron-affinic compound to its expected site of action, i.e., DNA, the potency of the compound as a radiosensitizer and chemosensitizer, as well as its hypoxic cell cytotoxicity, is greatly increased. Since mobility of the compound along the DNA backbone also is significant with respect to trapping radiation-induced radicals, and therefore improving radiosensitization, the development of DNA-affinic compounds that bind to DNA through non-covalent mechanisms (e.g., intercalation) is desirable.

However, compounds that bind non-covalently, but strongly, to DNA have slow dissociation kinetics. These compounds are potent cytotoxins because of mechanisms independent of bioreductive activation, e.g., by hindering the movement of polymerases or interfering with the action of topoisomerases I/II along the DNA backbone. Slow DNA dissociation kinetics can result in low hypoxic selectivity. Slow DNA dissociation kinetics can also be responsible for restricted extravascular diffusion of DNA-affinic compounds to hypoxic regions of tumors, therefore limiting the effectiveness of strong DNA-affinic compounds in vivo.

Thus, new DNA-affinic bioreductive compounds having greater mobility along the DNA backbone have been prepared. These new compounds exhibit improved radiosensitizing and chemosensitizing effectiveness, and an improved selective cytotoxicity towards hypoxic cells in vitro and in vivo. In general, the compounds of the present invention also exhibit improved therapeutic indices over prior sensitizers.

As discussed hereafter, it has been hypothesized, but not relied upon herein, that the improved radiosensitizing and chemosensitizing effects demonstrated by the present compounds are a result of disrupting the planarity of aromatic ring systems that are present in prior sensitizers, such as the substituted acridines disclosed in Papadopoulou-Rosenzweig et al. U.S. Pat. No. 5,294,715. The present hypoxia selective cytotoxins have a lower DNA-binding affinity than the acridine-based compounds because the present compounds are based: (1) either on a quinoline or quinoline-related aromatic system having substituents or (2) a nonaromatic ring system bonded to the b-ring of the quinoline or quinoline-related aromatic fused-ring system. In addition, the present compounds are weak bases having a greater lipophilicity than the acridine-based compounds, and therefore also exhibit enhanced cellular uptake for greater efficacy.

As also discussed hereafter, the present DNA-affinic compounds exhibit an improved hypoxia selective cytotoxicity and an improved radiosensitization and chemosensitization over the acridine-based compounds disclosed in Papadopoulou-Rosenzweig et al. U.S. Pat. No. 5,294,715 presumably because the present compounds intercalate less strongly with DNA. It has been found that the sensitizing efficacy and hypoxia selective cytotoxicity of compounds can be improved by reducing (i.e., hydrogenating) or eliminating the third aromatic ring of the acridine-based sensitizers. This improvement is attributed to intercalating DNA less strongly, therefore increasing the dissociation kinetics with DNA, and without influencing the appropriate one-electron reduction potential values. The present class of bioreductive agents therefore provides better adjuvant therapy in both radiotherapy and chemotherapy for solid tumor treatment.

In particular, the present invention is directed to a novel class of hypoxia selective cytotoxins and their use in radiation therapy and chemotherapy as sensitizers. In particular, hypoxia selective cytotoxins of the present invention have a general structural formula (I):

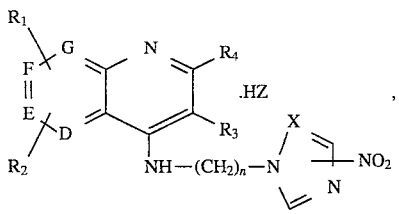

wherein D, E, F and G, independently, are carbon or nitrogen, with the proviso that three or more of D, E, F and G are carbon; $R_1$ and $R_2$, independently, are selected from the group consisting of methyl, halo, hydro, trifluoromethyl, methoxy, cyano and methylsulfo; $R_3$ and $R_4$, independently, are selected from the group consisting of methyl, ethyl, tertiary butyl, phenyl, naphthyl, halo, halomethylene (e.g., $FCH_2-$), hydro, trifluoromethyl, cyano and methylsulfo, or $R_3$ and $R_4$ taken together are a substituted or unsubstituted five or six-membered nonaromatic ring system; n is an integer 1 through 5; X is carbon or nitrogen; and Z is a physiologically acceptable anion.

Compounds having general structural formula (I) therefore have a fused ring system including two aromatic rings, wherein a nitrogen atom is present in at least one of the rings. The compounds of general structural formula (I) therefore are based on the structure of quinoline, which has structural formula (II):

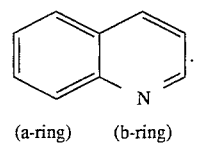

(a-ring)  (b-ring)

The benzo-ring is termed the a-ring of quinoline. The pyrido-ring is termed the b-ring of quinoline.

In addition to quinoline, other quinoline-related fused aromatic systems can be utilized in the present invention. Accordingly, D, E, F and G of the compound of general structural formula (I) can be, independently, carbon or nitrogen, provided that three or more of D, E, F and G are carbon. It should be understood that if D, E, F, or G is nitrogen, then the nitrogen is unsubstituted. In addition, if D, E, F, or G is carbon, and if $R_1$ or $R_2$ is not present on that carbon atom, then that carbon is bonded to a hydrogen atom.

Exemplary quinoline-related ring systems that can be used in addition to quinoline include, but are not limited to, fused ring systems having a structural formula (III) through (VI):

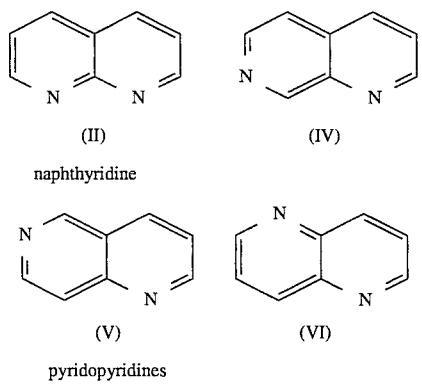

(II)        (IV)

naphthyridine (V)         (VI)

pyridopyridines

In accordance with an important feature of the present invention, $R_1$ and $R_2$ can be any organic substituent group that does not adversely affect the hypoxia selective cytotoxicity, radiosensitizing capabilities or chemosensitizing capabilities of the compound of general structural formula (I). Accordingly, $R_1$ and $R_2$, independently, can be, but are not limited to, hydro, i.e., hydrogen; methyl; halo, i.e., chloro, bromo, iodo or fluoro; trifluoromethyl; methoxy; cyano; or methylsulfo. Preferred $R_1$ and $R_2$ groups are hydro, chloro, fluoro, methyl, methoxy, and trifluoromethyl.

Substituent groups $R_3$ and $R_4$ bonded to the nitrogen-containing b-ring of the quinoline or quinoline-related aromatic fused ring system can be for example, but are not limited to, hydro; methyl; ethyl; tertiary butyl; phenyl; naphthyl; halomethylene; halo, i.e., chloro, bromo or iodo; cyano; and methylsulfo.

In addition, $R_3$ and $R_4$ can be taken together to form a substituted or unsubstituted five or six-membered nonaromatic ring system. The nonaromatic ring system can include heteroatoms, such as sulfur, oxygen or nitrogen. In nonaromatic ring systems including a nitrogen atom, the nitrogen atom has a methyl or ethyl group as a substituent.

Exemplary ring systems derived from combining substituents $R_3$ and $R_4$ include, but are not limited to, the nonaromatic ring systems illustrated in structural formulae (VII)–(XIV):

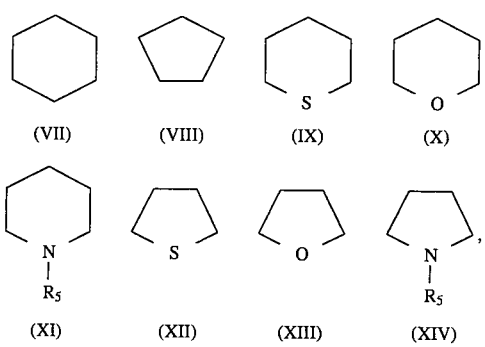

wherein R₅ is an alkyl group having one or two carbon atoms (i.e., methyl or ethyl).

Preferred R₃ and R₄ groups are hydro, halo, methyl, ethyl, phenyl, naphthyl, and trifluoromethyl. To achieve the full advantage of the present invention, R₃ and R₄ are taken together to form a nonaromatic five or six-membered ring, either carbocyclic or incorporating an oxygen atom, a sulfur atom or a nitrogen atom.

In accordance with an important feature of the present invention, the following are preferred combinations of the $R_1$ and $R_2$ substituents:

| $R^1$ | $R^2$ |
|---|---|
| H | H |
| CF₃ | H |
| CH₃ | H |
| CH₃ | CH₃ |
| F | H |
| F | F |
| CH₃O | H |
| CH₃O | CH₃O |
| Cl | H |
| Cl | Cl |

Similarly, the following are preferred combinations of the $R_3$ and $R_4$ substituents:

| $R^3$ | $R^4$ |
|---|---|
| H | H |
| H | CH₃ |
| CH₃ | CH₃ |
| H | CH₃CH₂ |
| H | CF₃ |
| H | CMe₃ |
| H | Naph |
| H | Cl |
| H | Ph | wherein CMe₃ is tert-butyl, Naph is naphthyl and Ph is phenyl.

In accordance with another important feature of the present invention, the following are preferred nonaromatic ring systems when R₃ and R₄ are taken together to form a nonaromatic five or six-membered ring:

—(CH₂)₃—
—CHMe(CH₂)₂—
—CH₂CHMeCH₂—
—(CH₂)₂CHMe—
—(CH₂)₄—
—CHMe(CH₂)₃—
—CH₂CHMe(CH₂)₂—
—(CH₂)₂CHMeCH₂—
—(CH₂)₃CHMe—
—SCH₂CH₂—
—CH₂SCH₂—
—CH₂SCH₂CH₂—
—CH₂OCH₂—
—CH₂OCH₂CH₂—
—CH₂NR₅CH₂CH₂—
—(CH₂)₃NR₅—
—(CH₂)₂NR₅—, wherein Me is methyl and R₅ is methyl or ethyl.

In the compound of general structural formula (I), the fused aromatic ring system is linked to a five-membered, nitrogen-containing aromatic heterocyclic ring by a methylene chain including one to five (i.e., n is an integer one through five) methylene (i.e., CH₂) groups. Preferably, the number of methylene groups is two to four, i.e., n is an integer two through four. The five-membered nitrogen-containing aromatic heterocyclic ring is based on imidazole and has one nitro group (NO₂) as a substituent. Imidazole has the structure (XV):

and is depicted in the compound of general structural formula (I) when X is carbon.

In addition to imidazole, however, another nitrogen-containing, five-membered aromatic ring also is useful in the present invention, as depicted in the compound of structural formula (I) when X is nitrogen. This five-membered aromatic ring is depicted in structural formula (XVI).

1,2,4-triazole

The hypoxia selective cytotoxins of general structural formula (I) are salts provided by adding an acid to the neutral compound. The salt form of the present compounds is depicted in structural formula (I). Conventionally, the salt form is used to increase sensitizer concentration along the DNA-backbone because of electrostatic attraction between the positively-charged compound of structural formula (I) and the negatively-charged phosphate moieties of DNA. The salt form is used to facilitate administration of the compound of structural formula (I) because the salt is more soluble in water or saline than the neutral form of the compound.

However, the neutral form of the compound depicted in general structural formula (I) also is useful as a hypoxia selective cytotoxin and as a radio-or chemosensitizer. The neutral form of the present compounds also can be used to intercalate with DNA and therefore act as sensitizers. The neutral form of the present compounds is protonated in vivo after administration to provide the salt form of the compound. The neutral form of the compound of general structural formula (I) is protonated at physiological pH (e.g., about 7) because the compounds are weak bases having a $pK_a$ of about 9.5 to about 10. The neutral form of the present class of hypoxia selective cytotoxins has general structural formula (XVII):

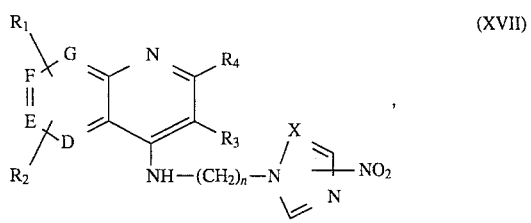

wherein D, E, F, G, X, Y, n and $R_1$–$R_4$ have the definitions previously set forth.

When preparing a compound of general structural formula (I), the neutral compound of structural formula (XVII) first is prepared. The neutral compound of structural formula (XVII) then is neutralized with an acid having a physiologically-acceptable anion. Accordingly, the acid (i.e., HZ) can be, but is not limited to, hydrochloric acid, phosphoric acid, nitric acid, perchloric acid, tetrafluoroboric acid, sulfuric acid, or a mixture thereof. Accordingly, the component Z in structural formula (I) can be, but is not limited to, chloride, bisulfate, dihydrogen phosphate, nitrate, perchlorate, tetrafluoroborate, or a mixture thereof.

Synthesis of exemplary novel compounds of the present invention is illustrated diagrammatically in the following schematic synthetic sequence which sets forth the method of synthesizing the compounds THNLA-1, S-THNLA-1, MeN-THNLA-1 and NLCPQ-1.

The following is a list of abbreviations used hereafter:

THNLA-1: 9-[3-(2-nitro-1-imidazolyl)propylamino]-1,2,3,4-tetrahydroacridine hydrochloride;

S-THNLA-1: 10-[3-(2-nitroimidazolyl)propylamino]-3,4-dihydro-1-H-thiopyrano[4,3-b]quinoline hydrochloride;

MeN-THNLA-1: 10-[3-(2-nitroimidazolyl)propylamino]-2-methyl-1,2,3,4-tetrahydro-benzo[b]-1,6-naphthyridine hydrochloride;

NLCPQ-1: 9-[3-(2-nitroimidazolyl)propylamino]-cyclopenten[b]quinoline hydrochloride;

NLA-1: 9-[3-(2-nitro-1-imidazolyl)propylamino]acridine hydrochloride;

NaI: sodium iodide;

PhOH: phenol;

HCl: hydrochloric acid;

POCl$_3$: phosphorous oxychloride;

ATP: adenosine triphosphate;

NaOH: sodium hydroxide;

TRIS-HCl: Tris(hydroxymethyl)aminomethane hydrochloride;

EDTA: ethylenediaminetetraacetic acid;

NH$_4$Cl: ammonium chloride;

MgCl$_2$: magnesium chloride;

CHCl$_3$: chloroform;

DMSO: dimethyl sulfoxide;

NH$_2$NH$_2$.H$_2$O: hydrazine hydrate;

Me: methyl;

eq: equivalents

OER: oxygen enhancement ratio, i.e., the ratio of a radiation dose required to reduce the survival fraction of hypoxic cells to a predetermined level (i.e., 1% of the control) compared to the radiation dose required to attain the same survival fraction in air;

SER: sensitization enhancement ratio, i.e., the ratio of the radiation dose required to reduce the survival fraction of hypoxic cells to a predetermined level (e.g., 1% of the control) compared to the radiation dose required to attain the same survival fraction with a sensitizer present;

$C_{1.6}$: concentration of a sensitizer yielding an SER of 1.6;

$C_i$: intracellular concentration;

$C_e$: extracellular concentration;

$C_{1.6i}$: intracellular concentration at $C_{1.6}$;

$IC_{50/H,1h}$: concentration for 50% inhibition of clonogenicity under hypoxia for 1 hour;

$IC_{50/A,1h}$: concentration for 50% inhibition of clonogenicity under aerobic conditions for 1 hour;

ThI: therapeutic index;

IsD: isoeffective to the oxygen dose;

$PC_{o/w}$: partition coefficient in octanol/water;

RT: room temperature; and

TLC: thin layer chromatography.

All commercial reagents were obtained from Aldrich Co., Milwaukee, Wis., or Eastman Kodak Co., Kingsport, Tenn. and were utilized without further purification.

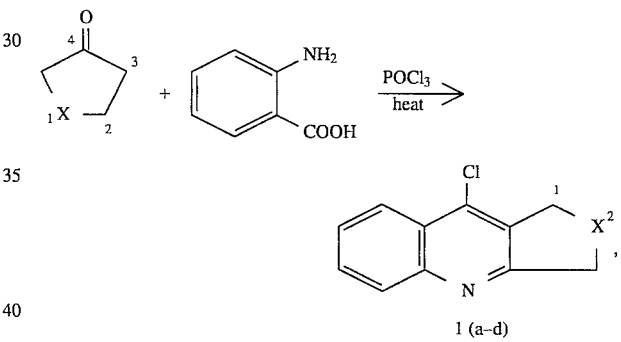

wherein

X=—[CH$_2$]$_2$—:1a

X=—SCH$_2$—:1b

X=—MeNCH$_2$—:1c

X=—CH$_2$—:1d, and wherein the heteroatom in compounds 1 (b,c) is in the 2-position, whereas in original cycloketone the carbonyl is in the 4-position.

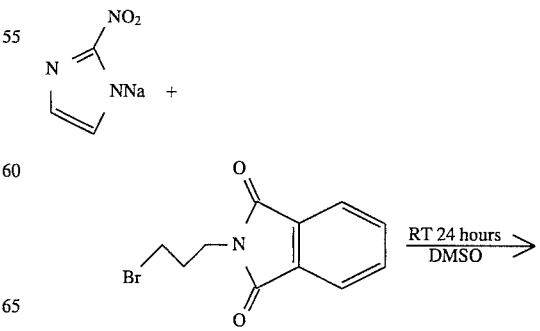

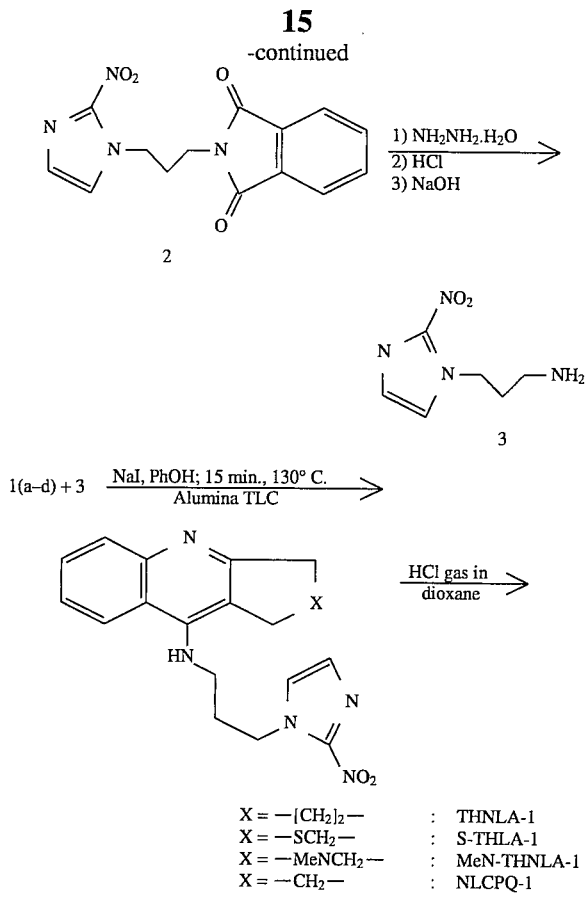

2,131,020, *Chemical Abstracts*, 102, page 6489n (1985), incorporated herein by reference. In particular, compound 2 of the synthetic sequence (150 mg) and hydrazine monohydrate (25 mg, 98% pure) were refluxed in 2 ml of ethanol for about 4.5 to about 5 hours. The reaction mixture then was cooled and acidified with excess 1N HCl solution. Next, the acidified solution again was refluxed for 1 hour, then cooled. The resulting insoluble phthalylhydrazide, a by-product, was filtered from the reaction mixture, and the ethanol was removed by evaporation under reduced pressure. The resulting mixture was filtered again to remove the remaining phthalylhydrazide, then alkalized with NaOH, and finally extracted ten times with $CH_2Cl_2$. The organic layer was dried over $Na_2SO_4$, filtered, then evaporated under reduced pressure to provide 3-(2-nitro-1-imidazolyl)propylamine, i.e., compound 3 of the synthetic sequence.

The 3-(2-nitro-1-imidazolyl)propylamine was a yellow oil which turned orange over time, and was obtained in a yield of about 70%. Analysis of compound 3 provided the following data: $^1$H NMR (CDCl$_3$) δ: 1.35 (br, 2H); 1.95 (q,J=6.96 Hz, 2H); 2.74 (t,J=6.54 Hz, 2H); 4.53 (t,J=7 Hz, 2H); 7.11 (s, 1H); 7.15 (s, 1H); MS:m/z of 170 (M+).

Compound 1a in the synthetic scheme was prepared from anthranilic acid and cyclohexanone by heating a mixture of the compounds in POCl$_3$, as set forth in M. Yamato et al., *J. Med. Chem.*, 32, pages 1295–1300 (1989), incorporated herein by reference.

Compound 1a (i.e., 9-chloro-1,2,3,4-tetrahydroacridine) and 3-(2-nitro-1-imidazolyl)propylamine (compound 3) were admixed and heated in PhOH (1.05 eq) and NaI (0.024 eq) at 130° C. for 15 min (minutes) in a preheated oil bath. The resulting THNLA-1 was purified by preparative TLC (alumina, ethyl acetate, optimum yield 32%), then converted to the hydrochloride salt with HCl gas in dioxane.

The hydrochloride salt of THNLA-1 was recrystallized from an ethanol:ethyl acetate mixture as a white solid, having a water solubility of about 12mM, yield 88%. Analysis of THNLA-1 provided the following data: mp 175°–180° C. (dec.); $^1$H NMR (GEN-500, 500 MHz spectrometer) (D$_2$O) δ: 8.06 (d,J=8.5 Hz, 1H), 7.79 (t,J=7.8 Hz, 1H), 7.65 (d,J=8.5 Hz, 1H), 7.48 (t,J =7.8 Hz, 1H), 7.32 (s, 1H), 6.99 (s, 1H), 4.54 (t,J=7.0 Hz, 2H), 4.08 (t,J=6.0 Hz, 2H), 2.92 (m, 2H), 2.38 (m, 4H), 1.87 (m, 4H). HRMS (VG 70-250SE mass spectrometer): Calcd for $C_{19}H_{21}N_5O_2$ (free amine):m/z 351.1695. Found: 351.1703.

THNLA-1 was prepared as an aqueous solution and then diluted to appropriate concentrations with tissue culture medium.

EXAMPLE 1

Preparation of THNLA-1

The nitroimidazolylalkyl phthalimide depicted as compound 2 in the above synthetic scheme was prepared by first dissolving 120 mg (milligram) of nitroimidazole in 5 ml (milliliter) dry DMSO, then slowly adding, with stirring, 42.47 mg NaH (sodium hydride, 60% dispersion in mineral oil) under a dry argon or nitrogen atmosphere to prepare the sodium salt of nitroimidazole. After the reaction mixture became clear, 290.4 mg of 3-bromopropylphthalimide (98% pure) was added in one portion to the sodium nitroimidazole solution, and the resulting mixture was stirred at room temperature for about 24 hours. After the 3-bromopropylphthalimide was consumed, as determined by TLC, the DMSO was removed by distillation under reduced pressure. The resulting residue then was triturated with a methylene chloride/water (CH$_2$Cl$_2$/H$_2$O) mixture. The resulting organic layer was dried over sodium sulfate (Na$_2$SO$_4$), and then filtered, and evaporated. The resulting product was identified as compound 2 by $^1$H NMR and HRMS.

Compound 2, i.e., 3-(2-nitro-1-imidazolyl)propylphthalimide, was a white solid obtained in a yield of about 82%. Analysis of compound 2 provided the following data: m.p. 151°–153° C. (Mel-Temp II open capillary melting point apparatus); $^1$H NMR (CDCl$_3$) δ: 2.27 (q,J=6.5 Hz, 2H); 3.78 (t,J=6 Hz, 2H); 4.53 (t,J=7 Hz, 2H); 7.16 (s, 1H); 7.36 (s, 1H); 7.73–7.90 (m, 4H); HRMS m/z 300.0842 calculated for $C_{14}H_{12}N_4O_4$; Found: 300.0841.

Compound 3 depicted in the above synthetic sequence was prepared in accordance with the modified hydrazinolysis method described in G. E. Adams et al., UK Pat. Appl.

EXAMPLE 2

Preparation of S-THNLA-1

Compounds 2 and 3 of the above synthetic scheme were prepared in the identical manner described in Example 1. Compound 1b was prepared by heating anthranilic acid and tetrahydrothiopyran-4-one in POC$_3$ in an identical manner as described in Example 1.

Compound 1b (i.e., 10-chloro-3,4-dihydro-1H-thiopyrano [4,3-b]quinoline) and 3-(2-nitro-1-imidazoyl)propylamine (compound 3) were reacted as set forth in Example 1 to provide S-THNLA-1. S-THNLA-1 was purified by preparative TLC (alumina, ethyl acetate, optimum yield 27%), then converted to the hydrochloride salt with HCl gas in dioxane.

The hydrochloride salt of S-THNLA-1 was recrystallized from an ethanol:ethyl acetate mixture as a white solid having the water solubility of about 9.5 mM, yield 55%. Analysis of S-THNLA-1 provided the following data: $^1$H NMR (GEN-500, 500 MHz spectrometer) (D$_2$O) δ: 8.06 (d,J=8.7 Hz, 1H), 7.85 (t,J=8 Hz, 1H), 7.69 (d,J=8.7 Hz, 1H), 7.54 (t,J=8 Hz, 1H), 7.35 (s, 1H), 6.98 (s, 1H), 4.54 (t,J=7.5 Hz, 2H), 4.04 (t,J=6.5 Hz, 2H), 3.63 (s, 2H), 3.28 (t,J=6.5 Hz, 2H), 3.08 (t,J=6.5 Hz, 2H), 2.40 (m, 2H). HRMS (VG 70-250SE mass spectrometer):Calcd. for $C_{18}H_{19}N_5O_2S$ (free amine) :m/z 369.125946. Found: 369.1262.

EXAMPLE 3

Preparation of MeN-THNLA-1

Compounds 2 and 3 of the above synthetic scheme were prepared in the identical manner described in Example 1. Compound 1c was prepared by heating anthranilic acid and 1-methyl-4-piperidone in POCl$_3$ in an identical manner as described in Example 1.

Compound 1c (i.e., 10-chloro-2-methyl-1,2,3,4-tetrahydro-benzo[b]-1,6-naphthyridine) and 3(2-nitro-1-imidazolyl)propylamine (compound 3) were reacted as set forth in Example 1 to provide MeN-THNLA-1. MeN-THNLA-1 was purified by preparative TLC (alumina, ethyl acetate, optimum yield 22%), then converted to the hydrochloride salt with HCl gas in dioxane. The hydrochloride salt of MeN-THNLA-1 was recrystallized from an ethanol:ethyl acetate mixture as a white solid having a water solubility of about 20 mM, yield 86%. Analysis of MeN-THNLA-1 provided the following data: $^1$H NMR (GEN-500, 500 MHz spectrometer) (CDCl$_3$) free amine, δ: 8.00 (d,J=8 Hz, 1H), 7.91 (d,J =8 Hz, 1H), 7.66 (t,J=7 Hz, 1H), 7.45 (t,J=7 Hz, 1H), 7.2 (s, 1H), 7.04 (s, 1H), 4.57 (t,J=6.8 Hz, 2H), 3.67 (s, 2H), 3.55 (t,J=6 Hz, 2H), 3.28 (t,J=6 Hz, 2H), 2.88 (t,J=6 Hz, 2H), 2.61 (s, 3H), 2.28 (m, 2H). FAB in m-nitrobenzyl alcohol (VG 70-250SE mass spectrometer): Calcd. for $C_{19}H_{23}N_6O_2$ (monoprotonated form) MH+:m/z 367.1882. Found: 367.1819.

EXAMPLE 4

Preparation of NLCPQ-1

Compounds 2 and 3 of the above synthetic scheme were prepared in the identical manner described in Example 1. Compound 1d was prepared by heating anthranilic acid and cyclopentanone in POCl$_3$ in an identical manner as described in Example 1.

Compound 1d (9-chloro-cyclopenteno[b]quinoline) and 3-(2-nitro-1-imidazolyl)propylamine (compound 3) were reacted as set forth in Example 1 to provide NLCPQ-1. NLCPQ-1 was purified by preparative TLC (alumina, ethyl acetate, yield 26%), then converted to the hydrochloride salt with HCl gas in dioxane. The hydrochloride salt of NLCPQ-1 was recrystallized from an ethanol:ethyl acetate mixture as a white solid having a water solubility of about 11 mM, yield 87.5%. Analysis of NLCPQ-1 provided the following data: $^1$H NMR of free amine (GEN-500, 500 MHz spectrometer) (CDCl$_3$), δ: 7.98 (d,J=8 Hz, 1H), 7.86 (d,J=8 Hz, 1H), 7.65 (t,J=7.8 Hz, 1H), 7.48 (t,J=7.8 Hz, 1H), 7.23 (s, 1H), 7.13 (s, 1H), 4.65 (t,J=7.2 Hz, 2H), 3.77 (s, br, 2H), 3.2 (t,J=6.5 Hz, 2H), 3.13 (t,J=7.2 Hz, 2H), 2.32 (m, 2H), 2.21 (m, 2H). HRMS (VG 70-250SE mass spectrometer) :Calcd. for $C_{18}H_{19}N_5O_2$ (free amine) :m/z 337.15387. Found: 337.1539.

S-THNLA-1, MeN-THNLA-1 and NLCPQ-1 were prepared as aqueous solutions and then diluted to appropriate concentrations with tissue culture medium.

As indicated above, the novel compounds of the present invention are hypoxia selective cytotoxins with improved radio- and chemosensitizing properties. As illustrated hereafter, studies show that the present compounds bind less strongly to DNA through intercalation than prior sensitizers. This feature provides hypoxic sensitizers and cytotoxins of superior in vitro therapeutic index compared to the fully aromatic, acridine-based NLA-series of compounds disclosed in Papadopoulou-Rosenzweig et al. U.S. Pat. No. 5,294,715.

As illustrated hereafter, the cytotoxicity, radiosensitization, chemosensitization, uptake and interactions of THNLA-1, S-THNLA-1, MeN-THNLA-1 and NLCPQ-1 with DNA and topoisomerases I or II, were determined using V79 Chinese hamster lung cells under both aerobic or hypoxic conditions. As also illustrated hereafter, the novel compounds of the present invention, like THNLA-1, a 2-nitroimidazole tethered to 1,2,3,4-tetrahydroacridine, are not fully aromatic compounds, and are hypoxia selective cytotoxins and radiosensitizers having a lower DNA-binding affinity than the fully aromatic NLA-1 acridine analog. The fully-aromatic NLA compounds are illustrated in the structural formula (XVIII) for NLA-1. The reduced DNA-binding affinity of the present compounds has been attributed to disruption of the planarity of the aromatic acridine ring system in the NLA series of compounds. The disruption of planarity also allows the present compounds to exhibit a rapid extravascular diffusion in vivo and a better localization to tumors.

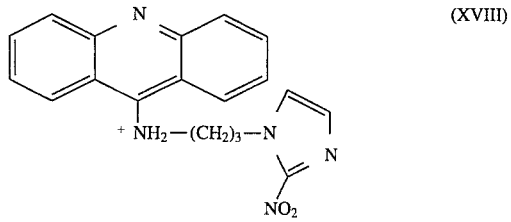

NLA-1 (prior art)

Samples of V79 Chinese hamster lung cells used in the following experiments were prepared as follows. V79 cells, exponentially growing as monolayer cultures in RPMI 1640 medium (Mediatech) supplemented with 10% fetal calf serum, were trypsinized, centrifuged for 5 min, harvested, then suspended in 25 ml Erlenmeyer flasks fitted with rubber caps at $5 \times 10^5$ cells/ml (5 ml). Individual flasks either were shaken (100 rpm) at 37° C. under aerobic conditions or made hypoxic by gassing with a 95% N$_2$ (nitrogen)/5% CO$_2$ (carbon dioxide) humidified gas mixture for 1 hour. In the various tests, a bioreductive compound of the present invention, such as THNLA-1, was added to a flask containing the aerobic or hypoxic V79 cells.

The acute aerobic and hypoxic cytotoxicity of THNLA-1, S-THNLA-1, MeN-THNLA-1 and NLCPQ-1 were determined by exposing samples of V79 cells for 1 hour at 37° C. under either hypoxic or aerobic conditions to a sensitizer concentration of 0 to 0.8 mM (millimolar) (FIGS. 1B and 2), and by a one through five hour exposure to a fixed THNLA concentration (e.g., 100 μM (micromolar), FIG. 1A). To determine the fraction of surviving cells, samples were removed, diluted and plated to provide $2 \times 10^2$ to $2 \times 10^4$ cells/well on 60 mm Linbro multi-well plates (Flow Laboratories, McLean, Virginia). The plates were incubated at 37° C. for 6 days, stained with crystal violet and examined for colony formation. Colonies of 50 cells or greater were counted. Each plotted point in FIGS. 1 and 2 represent the mean of three or four replicate experiments.

FIG. 1A shows that in the presence of 100 μM of THNLA-1, under aerobic conditions, a survival fraction of about 50% is observed after 3.5 hours, while the corresponding hypoxic survival was less than 0.002%. FIG. 1B illustrates the THNLA-1 concentration-dependent cytotoxicity under hypoxic/aerobic conditions after a 1 hour exposure at 37° C. FIG. 1B shows that THNLA-1 is substantially more toxic to V79 cells under hypoxic conditions than aerobic conditions. For example, to achieve a 10% survival fraction under hypoxic conditions, only about 0.1 mM of THNLA-1 is required. Under aerobic condition, about 0.475 mM of THNLA-1 is required to achieve a 10% survival fraction. The compounds of the present invention accordingly are hypoxia selective cytotoxins.

From the experiments illustrated in FIG. 1, the $IC_{50}$ values (concentration for 50% inhibition of determined for THNLA-1. The $IC_{50/A,1h}$ for THNLA-1 is clonogenicity) under hypoxia (H) or air (A) was about 360 μM and the $IC_{50/H,1h}$ is about 33 μM. Therefore, the differential aerobic/hypoxic toxicity ($IC_{50A}/IC_{50H}$) for THNLA-1 is about 11. The prior art fully-aromatic NLA-1 compound appears to be about a two times more potent hypoxic cytotoxin ($IC_{50/H,1h}$=15 μM) than THNLA-1, however, the selectivity of NLA-1 is 5.5, or two times smaller than THNLA-1. The in vitro therapeutic index (ThI, defined as $IC_{50/A, 1h}/C_{1.6}$) for THNLA-1 and NLA-1 are about 20 and about 11, respectively.

Figures 2A, 2B:
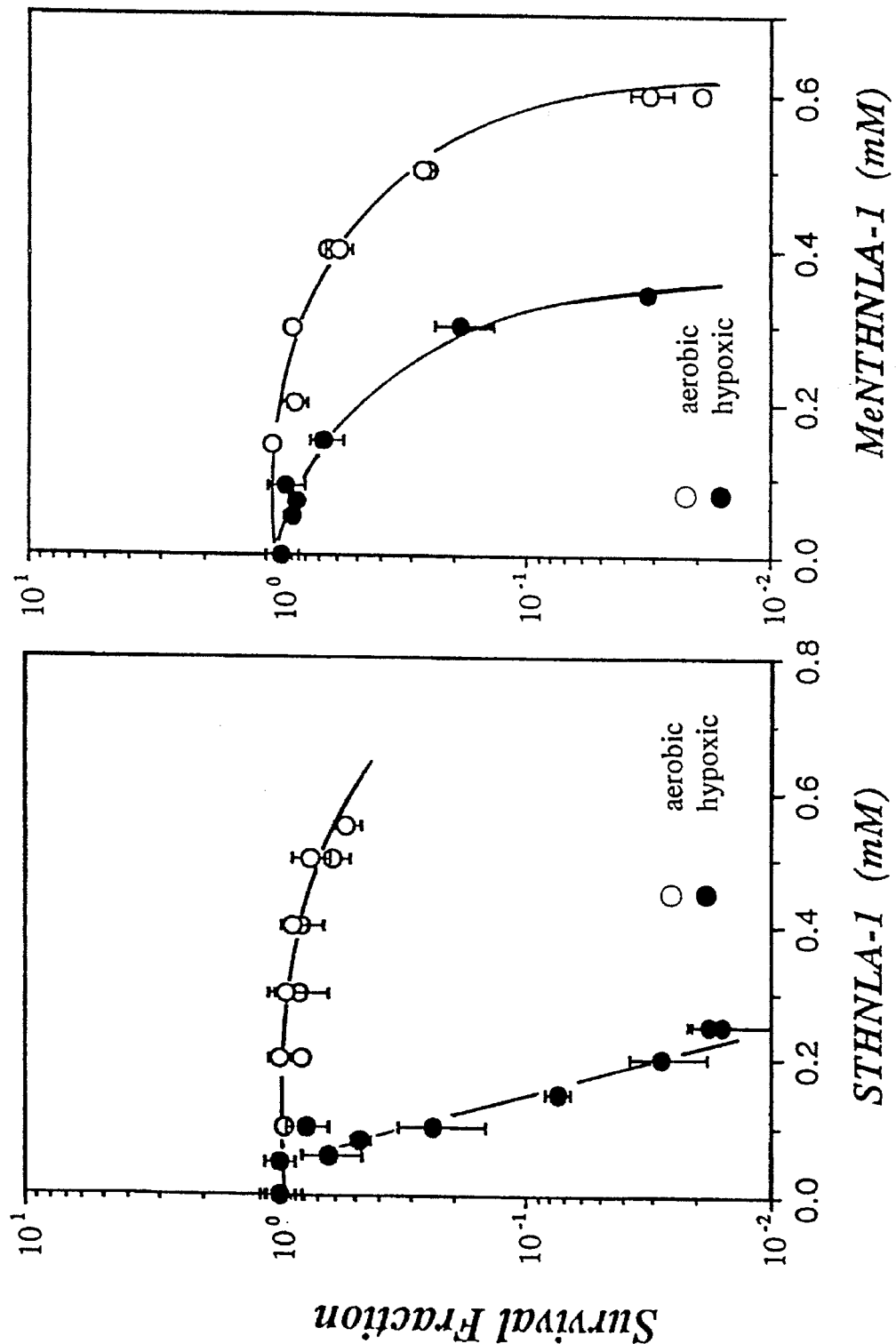
FIGS. 2A–C are plots of survival fraction of V79 cells vs. S-THNLA-1, MeN-THNLA-1 or NLCPQ-1 concentrations, respectively, after a one hour time period at 37° C. under aerobic or hypoxic conditions.
Figure 2C:
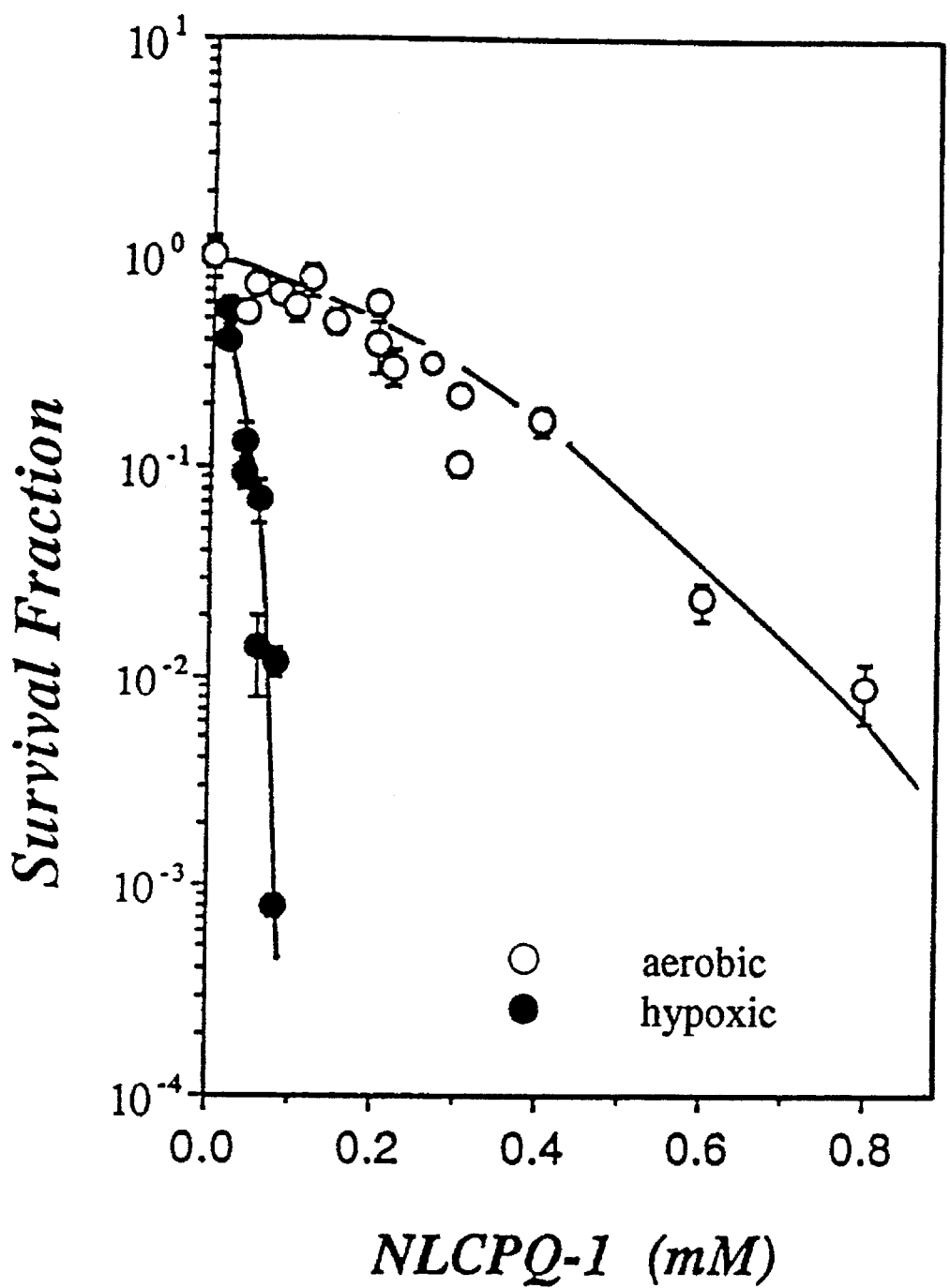

In FIG. 2, the concentration-dependent cytotoxicity for S-THNLA-1, MeN-THNLA-1 and NLCPQ I is plotted. From this data, a differential aerobic/hypoxic toxicity of 9, 2.2 and 8 was calculated for S-THNLA-1, MeN-THNLA I and NLCPQ-1, respectively. The corresponding ThI values for S-THNLA-1, MeN-THNLA-1 and NLCPQ-1 are about 15, 7 and 25, respectively.

Figure 4:
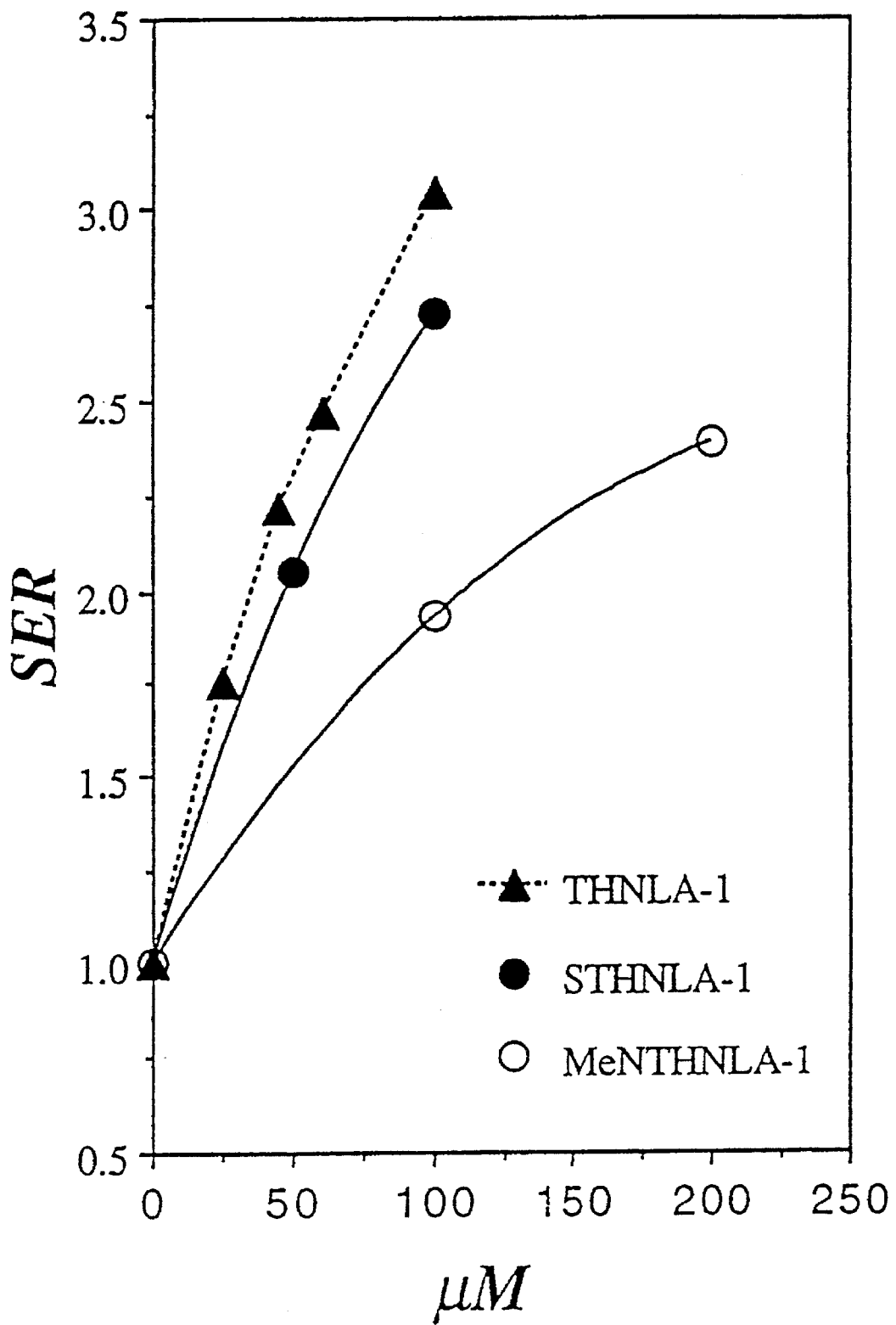
FIG. 4 is a plot of SER vs. THNLA-1, S-THNLA-1 and MeN-THNLA-1 concentration.

Radiosensitization studies were performed on V79 cells in a manner similar to the acute toxicity experiments, except that the survival fraction was determined after a predetermined radiation dose. THNLA-1 was added to aerated or hypoxic V79 cells at 37° C., 1 hour before irradiation at room temperature ($^{60}$Co, 1.534 Gy/min). One Gy is equal to 100 rads, wherein one rad is the quantity of ionizing radiation that results in the absorption of 100 ergs of energy per gram of irradiated material. Hypoxia was maintained throughout irradiation. Survival curves were normalized for the hypoxic cytotoxicity of THNLA-1 at a zero radiation dose (FIG. 3A). Sensitization enhancement ratios (SER) were determined at a 10% survival level. The $C_{1.6}$ value (i.e., a concentration of THNLA-1 yielding an SER of 1.6) was determined by plotting SER values against THNLA-1 concentration (FIG. 3B). The plotted points in FIGS. 3 and 4 represent the mean of 2 or 3 replicate experiments.

FIG. 3A shows that increasing the concentration of THNLA-1 from 0 to 100 μM substantially increases the response of hypoxic V79 cells to radiation. FIG. 3B shows that the SER for THNLA is about 3 for a THNLA-1 concentration of about 100 μM. The concentration dependence of the SER for THNLA-1, S-THNLA-1 and MeN-THNLA-1 is illustrated in FIG. 4.

Significant radiosensitization of hypoxic V79 cells was observed at room temperature, when the THNLA-1 was administered 1 hour at 37° C. before irradiation. Radiosensitization was not observed under aerobic conditions. In other experiments, radiosensitization also was not observed when THNLA-1 was administered immediately after irradiation. The degree of radiosensitization also is apparently concentration dependent and SER values tend to approach a plateau (FIGS. 3B and 4). Accordingly, optimal doses of the hypoxia selective compound of general structural formula (I) can be determined. For example, exposure to 100 μM THNLA-1 at 37° C. for 1 hour before irradiation at room temperature gave an SER of about 3, which is equivalent to the OER (after normalization for hypoxic toxicity). This concentration is not aerobically toxic (i.e., is about 28% of $IC_{50/A,1h}$). The $C_{1.6}$ value of THNLA is 19 μM. The $C_{1.6}$ values for S-THNLA-1, MeN-THNLA-1 and NLCPQ-1 are 40–45, 59 and 7 μM, respectively.

The isoeffective to the oxygen dose (IsD) at a constant radiation dose was determined by exposing aerobic or hypoxic V79 cells to variable concentrations of THNLA-1 or the prior art NLA-1 compound for 1 hour at 37° C., then to a predetermined radiation dose. The survival fraction under hypoxic conditions (plotted versus compound concentration) meets the aerobic survival fraction (radiation toxicity) at the IsD. The IsD value is a useful indicator of the overall potency of a compound as a sensitizer and cytotoxin of hypoxic cells. IsD is especially useful when comparing different compounds for hypoxic cytotoxicity and radiosensitizing efficacy.

Figures 5A, 5B:
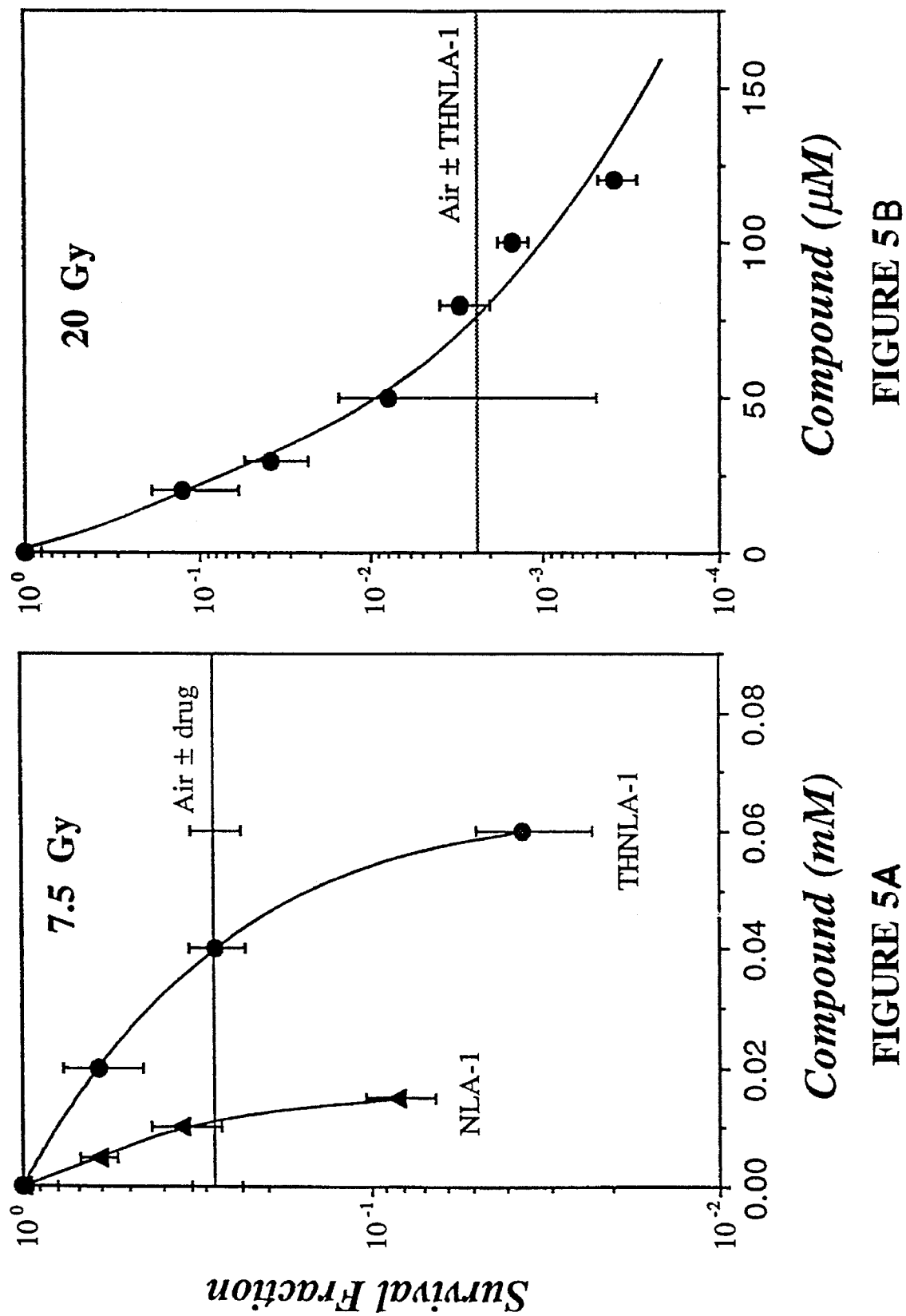
FIGS. 5A and 5B are plots of survival fraction vs. concentration of THNLA-1 or NLA-1 at a radiation dose of 7.5 Gy or 20 Gy under hypoxic or aerobic conditions.

FIGS. 5 and 6 illustrate the IsD at 7.5 Gy (FIG. 5A) and 20 Gy (FIG. 5B). FIGS. 5A and 6A include a comparison to the prior art NLA-1 compound. V79 cells were irradiated at 7.5 Gy or 20 Gy after a 1 hour exposure under hypoxia (symbols) or air (straight line), at various drug concentrations. No toxicity or radiosensitization for any tested compound was observed under aerobic conditions over the tested concentration ranges. IsD values were calculated from the intersections of the survival fractions of the hypoxic curves with the survival fraction in air. All data points in FIGS. 5 and 6 represent the mean of two replicate experiments.

In particular, FIGS. 5 and 6 illustrate that the IsD for THNLA-1 at 7.5 Gy and 20 Gy was about 40 and about 78 μM, respectively. The corresponding curves obtained under hypoxic conditions for the determination of IsD had a different shape at the two tested radiation doses. At the higher dose of 20 Gy, the initial shoulder, observed at 7.5 Gy, disappeared. For NLA-1, the IsD at 7.5 Gy was about 11 μM. For S-THNLA-1 and MeN-THNLA-1, the corresponding IsD at 20 Gy was about 103 and about 127 μM, respectively (FIG. 6B).

The partition coefficient of the hypoxia selective cytotoxins of the present invention were determined by the method of T. Fujita et al., *J. Am. Chem. Soc.*, 86, 5175–5180 (1964), incorporated herein by reference. The partition coefficient in octanol/water ($PC_{o/w}$) for THNLA-1 was 0.14 (versus 0.07 for NLA-1). Therefore, THNLA-1 is about two times more lipophilic than NLA-1 and about two times more hydrophilic than MISO (misonidazole). However, the increased lipophilicity of THNLA-1 did not result in an increase of the aerobic mean uptake factor (intracellular:extracellular concentration, $C_i/C_e$) of THNLA-1 compared to NLA-1.

Intracellular ($C_i$) and extracellular ($C_e$) drug concentrations were determined after exposing V79 cells ($2\times10^6$/ml, 5 ml) for 30 minutes at 37° C. to THNLA-1 concentrations of 0 to 500 μM under aerobic conditions. Also, uptake measurements at various times under both aerobic and hypoxic conditions were made. Afterwards, the samples were pelleted by centrifuging for 6 minutes at 0° C. A small volume of the supernatant (200 μl) was combined with 9 equal volumes (1.8 ml) of acetonitrile and the remaining supernatant was discarded. The samples were centrifuged again to remove residual supernatant and the pellets were lysed with 90 µl water and deproteinized with 0.9 ml acetonitrile. After centrifugation and filtration, all samples were stored at −70° C. until a UV spectroscopic analysis was made at two different wave lengths: 330 nm (nanometers) (absorption of the nitro-group) and 244 nm ($\lambda_{max}$). Samples including only V79 cells were treated in an identical manner for correction of the measurements, while a calibration curve was obtained by measuring the absorption of known concentrations of THNLA-1 in the same solvent system. Mean intracellular concentration of drug was calculated using a value of 810 fl as an intracellular water content of log-phase cells.

Figures 7A, 7B:
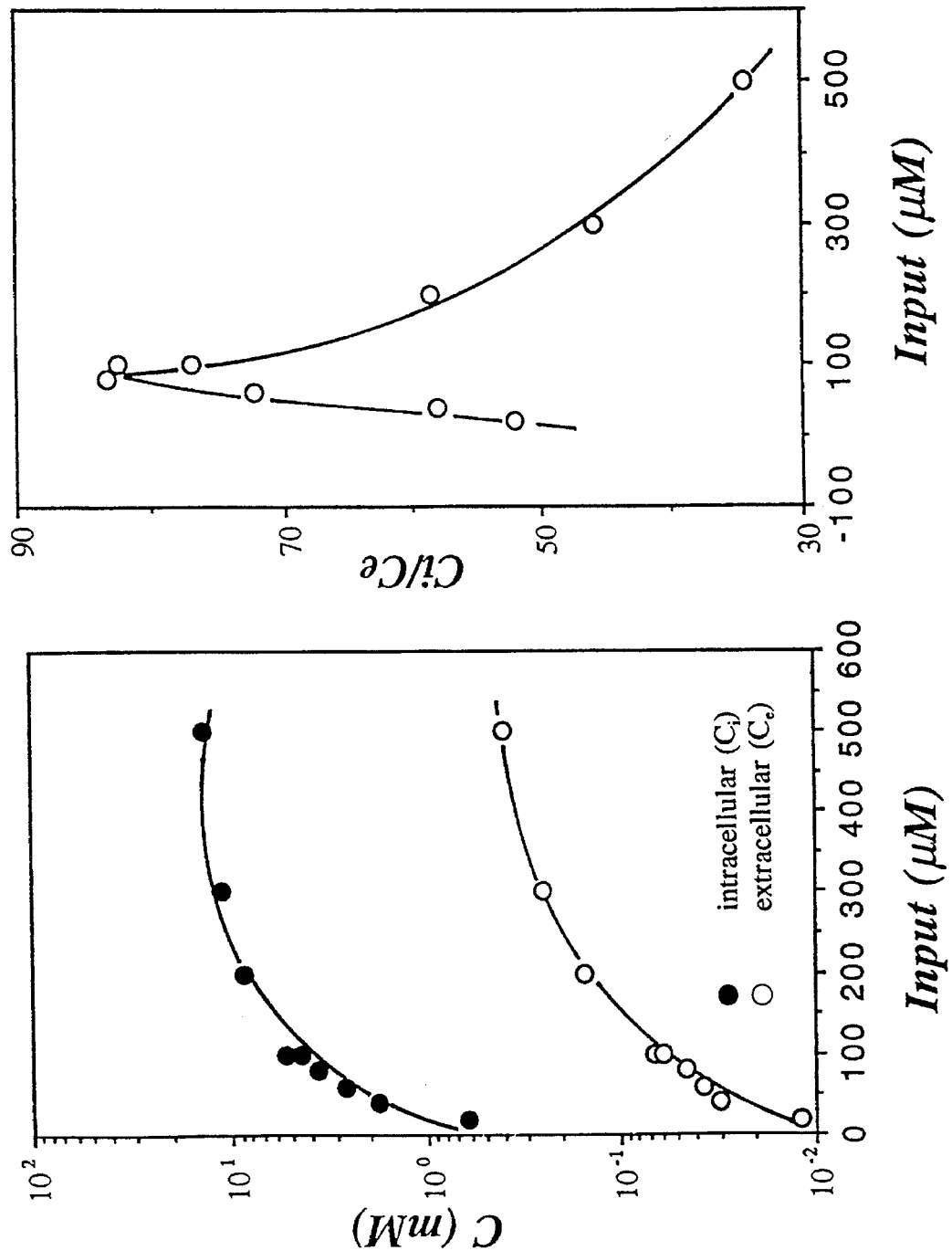
FIG. 7A is a plot of intracellular ($C_i$) and extracellular ($C_e$) concentrations of THNLA-1 vs. THNLA-1 input concentration.
FIG. 7B is a plot of $C_i/C_e$ (uptake factor) vs. THNLA-1 input concentrations under aerobic conditions for 30 minutes at 37° C.
Figure 7C:
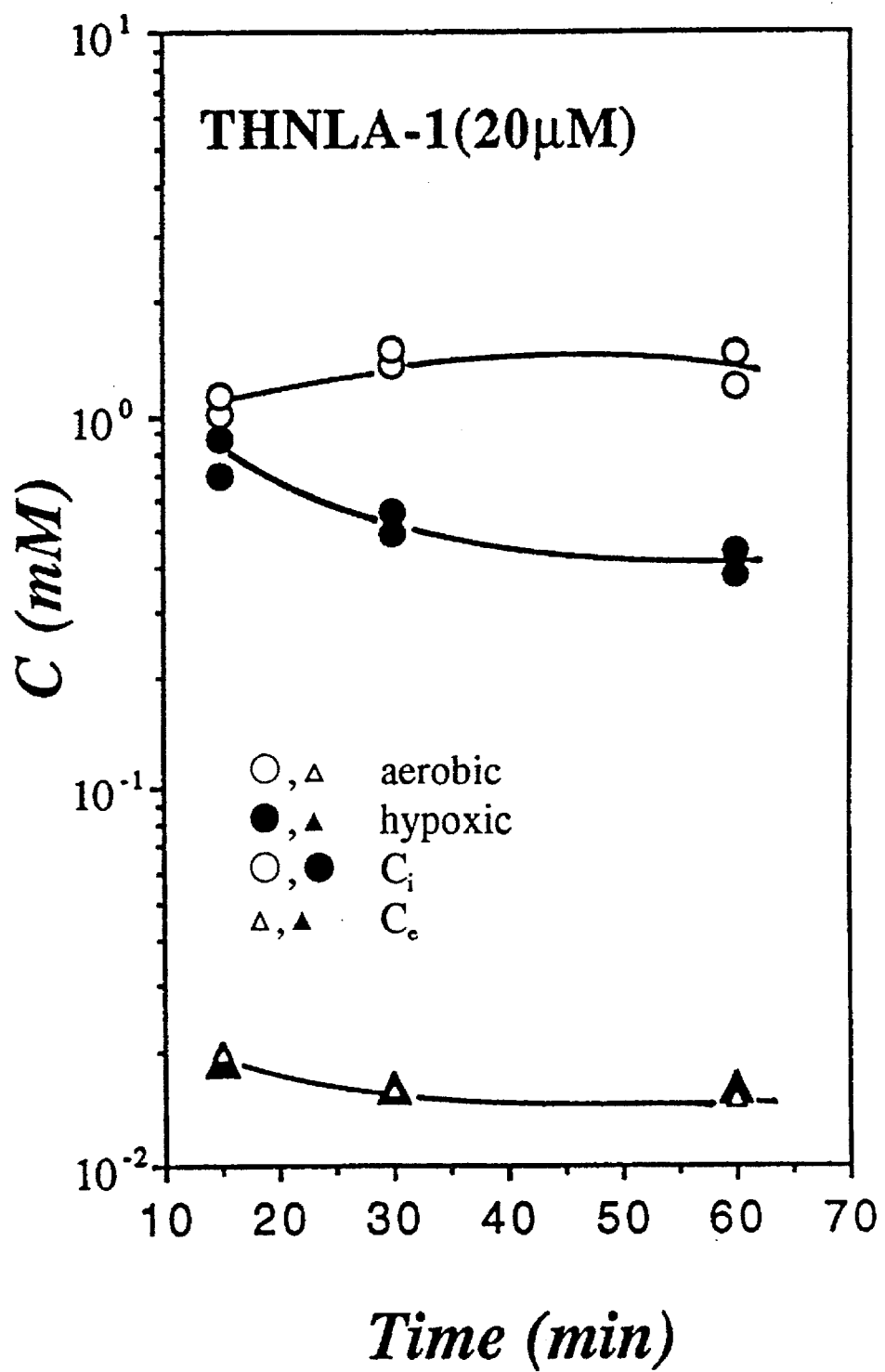
FIG. 7C is a plot of THNLA-1 uptake ($C_i$ and $C_e$) by V79 cells under aerobic or hypoxic conditions vs. time for a constant 20 μM (micromolar) concentration of THNLA-1 at 37° C.

FIG. 7A illustrates a comparison of mean intracellular ($C_i$) and extracellular ($C_e$) concentrations (in µM) of THNLA-1 over an input THNLA-1 concentration of 0 to 500 µM. FIG. 7B illustrates uptake factors (i.e., $C_i/C_e$) under aerobic conditions for 30 minutes at 37° C. over the same THNLA-1 input concentrations. FIG. 7C illustrates the uptake of THNLA-1 (20 µM) by aerobic and hypoxic V79 cells after a 15, 30 or 60 minute incubation time at 37° C. Concentrations were determined by UV spectrophotometry at 330 nm. The plotted points represent results from two experiments, in triplicate.

Changes in the intracellular accumulation of THNLA-1, as well as the corresponding extracellular concentration, by increasing the input concentration of THNLA-1 is illustrated in FIG. 7A. FIG. 7A shows that the intracellular concentration ($C_i$) of THNLA-1 is substantially greater than the corresponding extracellular concentration ($C_e$) of THNLA-1. FIG. 7B shows that the uptake factor ($C_i/C_e$) reaches a maximum at an input concentration of about 100 µM THNLA-1 and then starts to decrease. FIG. 7C illustrates that under hypoxic or aerobic conditions, the $C_i$ of THNLA-1 is substantially greater than the $C_e$.

In particular, the $C_i$ of THNLA-1 remained basically unchanged over 15, 30 and 60 minutes incubation periods under aerobic conditions, while a decrease of $C_i$ over time was observed under hypoxic conditions (FIG. 7C). This decrease is attributed to metabolism under hypoxic conditions. The intracellular concentration for an SER of 1.6 ($C_{1.6i}$) for THNLA-1 and NLA-1 are 0.443 and 0.885 mM, respectively.

Figure 8:
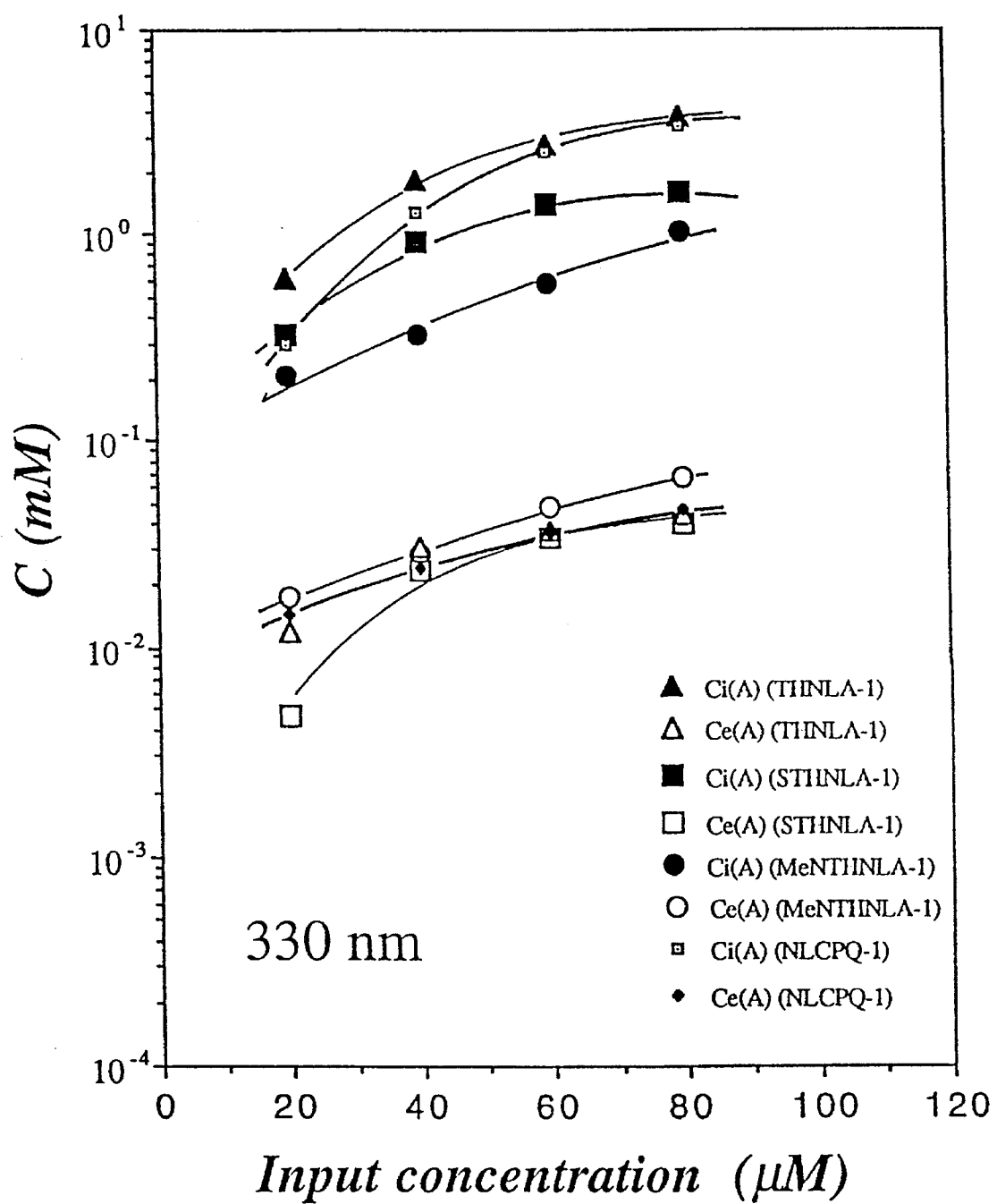
FIG. 8 is a plot of $C_i$ and $C_e$ vs. input concentrations of THNLA-1, S-THNLA-1, MeN-THNLA-1 and NLCPQ-1.

The $PC_{o/w}$ for S-THNLA-1, MeN-THNLA-1 and NLCPQ-1 were measured as 0.41, 0.40, and 0.30, respectively, showing the increased lipophilicity of S-THNLA-1, MeN-THNLA-1 and NLCPQ-1 over NLA-1. A comparison of the aerobic uptake by V79 cells for THNLA-1, S-THNLA-1, MeN-THNLA-1 and NLCPQ-1 is shown in FIG. 8.

Uptake measurements in the presence of the lysosomotropic agent ammonium chloride ($NH_4Cl$) also were performed in a manner as previously described. Ammonium chloride was added to the V79 cell samples at different concentration levels 15 minutes prior to THNLA-1 addition. The V79 cells then were incubated with 60 µM of THNLA-1 (or NLA-1) for 45 minutes under aerobic conditions at 37° C.

Figures 9A, 9B:
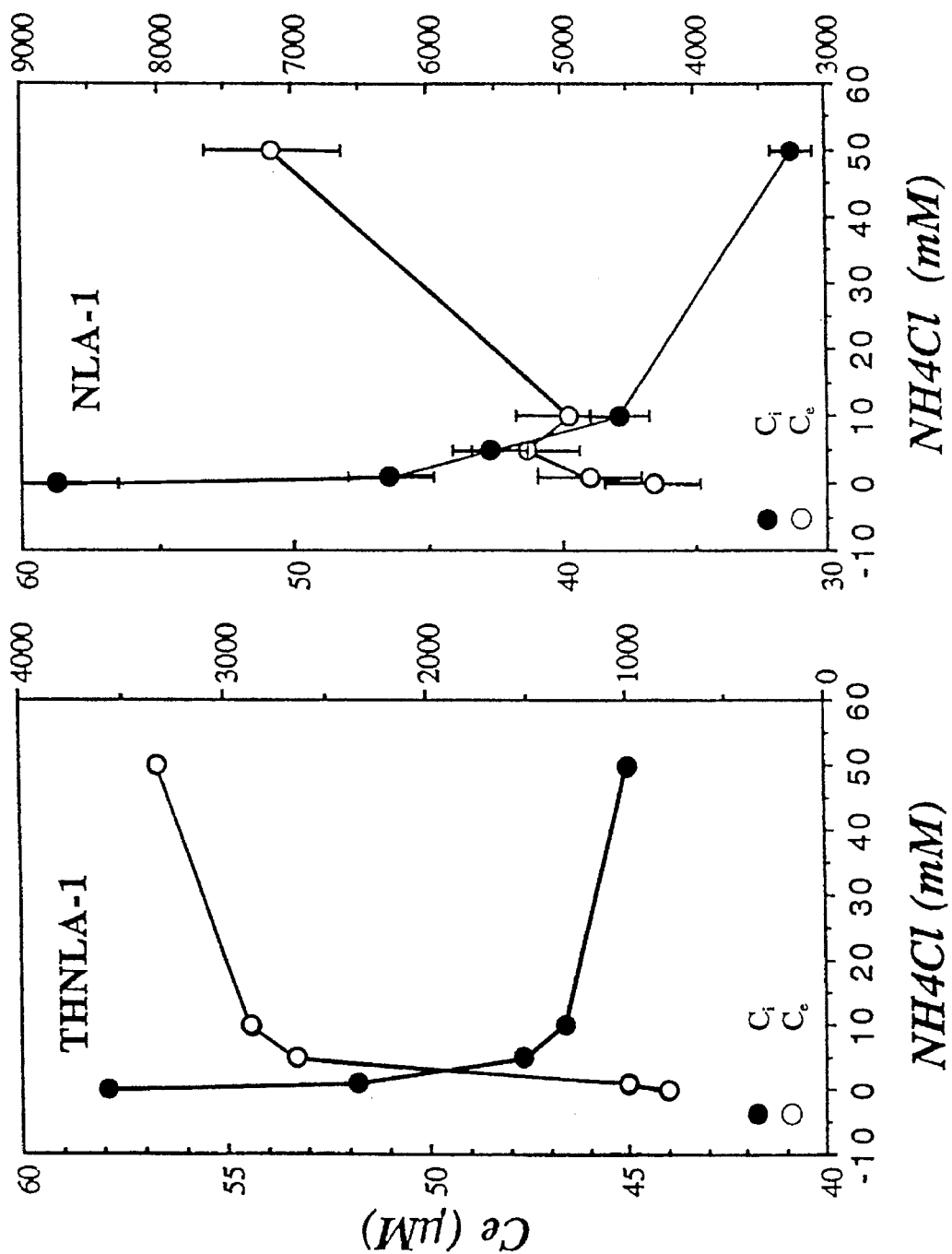
FIGS. 9A and 9B are plots of $C_e$ and $C_i$ (μM) of THNLA-1 and NLA-1, respectively, at 60 μM input concentration in aerobic V79 cells vs. ammonium chloride concentration (mM)
Figure 9C:
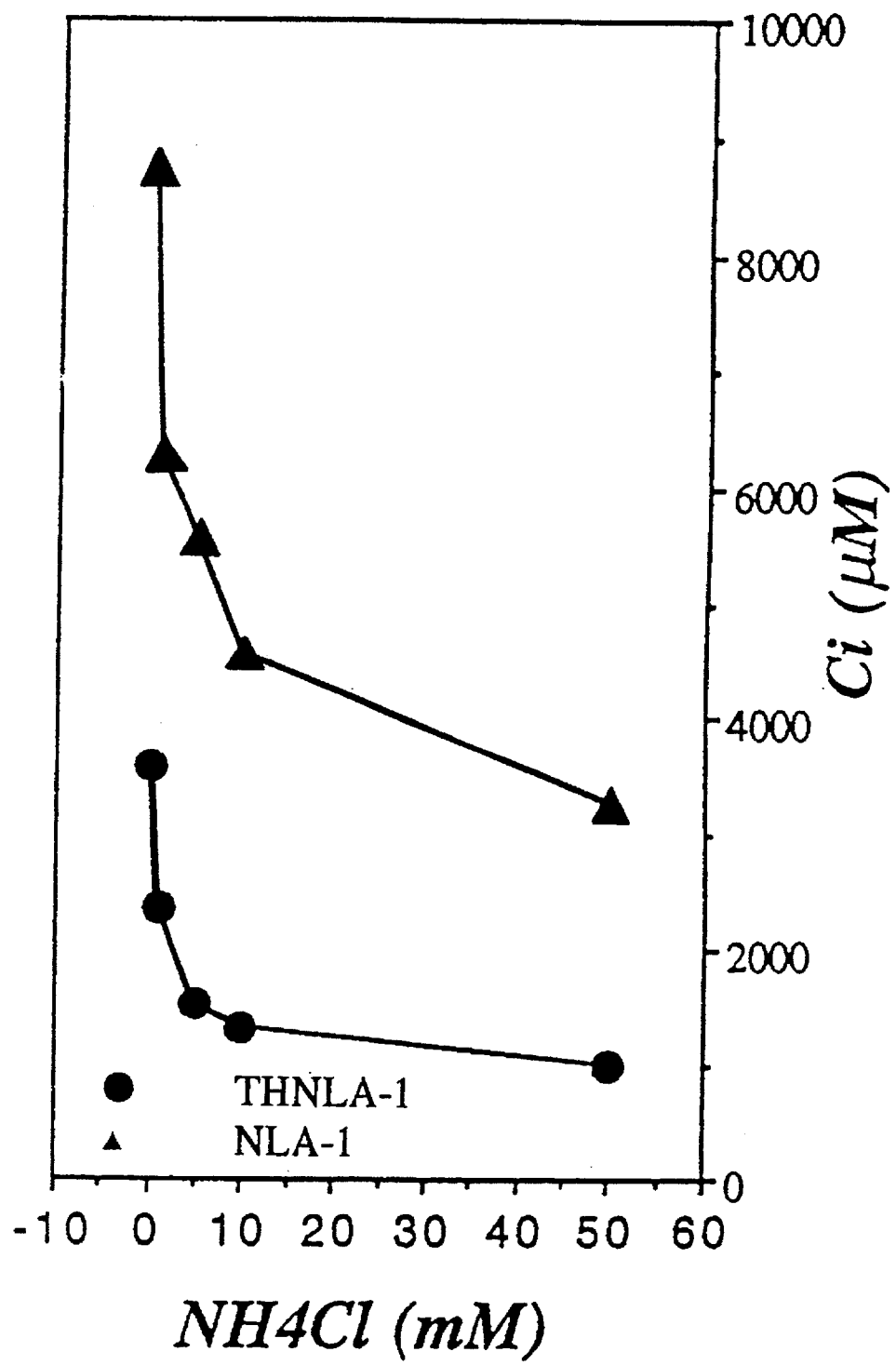
FIG. 9C is a plot of $C_i$ vs. ammonium chloride concentration comparing the effect of ammonium chloride on $C_i$ of THNLA-1 and NLA-1 in aerobic V79 cells.

FIG. 9 illustrates the effect of ammonium chloride on $C_i$ and $C_e$ concentration of THNLA-1 (FIG. 9A) or NLA-1 (FIG. 9B) at 60 µM input concentration in aerobic V79 cells. FIG. 9C compares the effect of ammonium chloride addition on the $C_i$ accumulation of THNLA-1 and NLA-1 at 60 µM input concentration in aerobic V79 cells. Concentrations were determined by UV spectrophotometry at 330 nm. The plotted points represent the mean of two experiments.

When V79 cells were incubated for 15 minutes with increasing concentrations of $NH_4Cl$ prior to THNLA-1 addition and under aerobic conditions, the intracellular concentration ($C_i$) of THNLA-1 was decreased significantly (i.e., a factor of about 3, at 50 mM $NH_4Cl$, FIG. 9A). The $C_i$ for the prior art compound NLA-1 also decreased by about a factor of 3 (FIG. 9B). A comparison of the aerobic uptake of the THNLA-1 and NLA-1 in the presence of $NH_4Cl$ is shown in FIG. 9C. A similar decrease in aerobic uptake was observed for S-THNLA-1 in the presence of $NH_4Cl$ (FIG. 10A). A comparison of the effect of $NH_4Cl$ on the aerobic uptake of THNLA-1, S-THNLA-1 and NLA-1 is depicted in FIG. 10B.

FIG. 11A illustrates the uptake reduction rates for THNLA-1 and NLA-1 (in µM per mM of $NH_4Cl$) over an increasing $NH_4Cl$ concentration range. FIG. 11B illustrates the correlation between $C_{1.6}$ values and corresponding $C_i/C_e$ values for NLA-1, THNLA-1, S-THNLA-1 and MeN-THNLA-1.

An agarose gel electrophoresis technique was used to determine whether THNLA-3 intercalates DNA. Compounds that strongly intercalate DNA retard DNA mobility during agarose gel electrophoresis due to unwinding and extension of the dsDNA. Agents that do not intercalate DNA, or that bind to DNA via other mechanisms, do not decrease DNA mobility in this assay.

In particular, a Topo I drug screening kit (TopoGEN, Inc., Columbus, Ohio) was used to assay the topoisomerase I THNLA-1 interaction. The tests were performed in a 20 µl (final volume) solution containing: water, assay buffer (10 mM Tris-HCl pH 7.5, 1 mM EDTA, 100 mM NaCl), 0.75 µg of supercoiled plasmid DNA, 6 units of calf thymus Topo I (in 50 mM Tris.HCl, pH 7.55, 0.7 M (molar) Nacl, 0.5 mM EDTA, 0.5 mM dithiothreitol, 10% glycerol) and various concentrations of THNLA-1 or 100 µM camptothecin for comparison. Camptothecin is a Topoisomerase I poison used as an anticancer drug. Camptothecin stabilizes the Topo I-DNA clearable complex, and therefore prevents the resealing of DNA by Topo-I.

Individual reaction n mixtures were heated for 30 minutes at 37° C. on a heating block, and then 2 µl of 10% SDS-proteinase K solution was added to each reaction mixture. The resulting reaction mixtures then were heated for an additional 30 minutes at 37° C. The reaction mixtures in a loading buffer were extracted with $CHCl_3$ prior to submarine electrophoresis on a 1% agarose gel. The DNA bands were observed visually by staining with ethidium bromide (0.5 µg/ml).

In the THNLA-1-topoisomerase I interaction test, supercoiled (sc) DNA was incubated either alone, in the presence of Topo I (2 units), or in the presence of Topo I (6 units) and inhibitor, i.e., camptothecin (100 µM) or THNLA-1 (100, 200, 400, 600, 800 or 1000 µM). Other incubated samples were scDNA and THNLA-1 (1000 µM) in the absence of Topo I, both unextracted and after extraction with $CHCl_3$. The results of the topoisomerase I test clearly showed that THNLA-1 inhibits Topo I-induced relaxation of supercoiled DNA, but at significantly higher concentrations than NLA-type compounds.

A Topo II assay kit (TopoGEN, Inc., Columbus, Ohio) also was used to assay the topoisomerase II -THNLA-1 interaction. The tests were performed on a 20 μl (final volume) solution containing: water, cleavage buffer (30 mM Tris.HCl, pH 7.6, 3 mM ATP, 15 mM 2-mercaptoethanol, 8 mM $MgCl_2$, 60 mM NaCl), 0.3 μg (microgram) of kinetoplast DNA [KDNA], 4 units of human Topo II and various concentrations of THNLA-1. Individual reaction mixtures were heated for 30 minutes at 37° C. on a heating block, and then 2 μl of a 10% SDS-proteinase K solution was added to each reaction mixture. The resulting reaction mixtures then were heated for an additional 30 minutes at 37° C. After addition of a 0.1 volume of loading buffer, the reaction mixtures were extracted with $CHCl_3$ prior to submarine electrophoresis on a 1% agarose gel containing ethidium bromide (0.5 μg/ml).

In the THNLA-1-Topoisomerase II interaction test, kinetoplast DNA (KDNA) was incubated either alone, in the presence of Topo II (4 units) or in the presence of Topo II and inhibitor, i.e., THNLA-1 (200, 400, 600, 800 or 1000 μM, respectively). Other incubated samples were KDNA and THNLA-1 (1000 μM) in the absence of Topo II, a linear KDNA marker, and a decatenated KDNA marker. The results of the Topoisomerase II assay clearly showed that THNLA-1 does not inhibit the Topo II-induced decatenation of KDNA even at very high concentrations, contrary to the NLA-compounds.

Contrary to the strong DNA-intercalating NLA-compounds, THNLA-1, S-THNLA-1 and MeN-THNLA-1 do not affect the mobility of supercoiled DNA on the electrophoretic gel up to millimolar concentrations. Accordingly, the hypoxia selective cytotoxins of the present invention have been shown to bind less efficiently to DNA. Even though THNLA-1 initiates inhibition of supercoiled DNA relaxation, induced by Topo I, at 100 μM concentration, complete inhibition was not observed at THNLA-1 concentrations even up to 1 mM. The observed inhibition is attributed to either unwinding of DNA through intercalation or direct interaction with the Topo I. THNLA-1 also did not inhibit decatenation of kinetoplast DNA [KDNA] induced by topoisomerase II up to a 1 mM concentration of THNLA-1.

S-THNLA-1 and MeN-THNLA-1 also did not inhibit the action of Topoisomerase II on kinetoplast DNA up to a 1 mM concentration. The action of Topoisomerase I on closed circular DNA was completely inhibited when about 800 μM of S-THNLA-1 was used. In addition, some nicked DNA also was observed. However, S-THNLA-1 alone also caused the formation of some nicked DNA at a concentration of 800 μM. MeN-THNLA-1, in concentrations of up to 1000 μM, only partially inhibited Topo I, and no formation of nicked DNA was observed.

The physicochemical and biological properties of THNLA-1 are summarized and compared to NLA-1 in Table I. The physicochemical and biological properties of S-THNLA-1, MeN-THNLA-1 and NLCPQ-1 are summarized in Table II.

Figure 10:
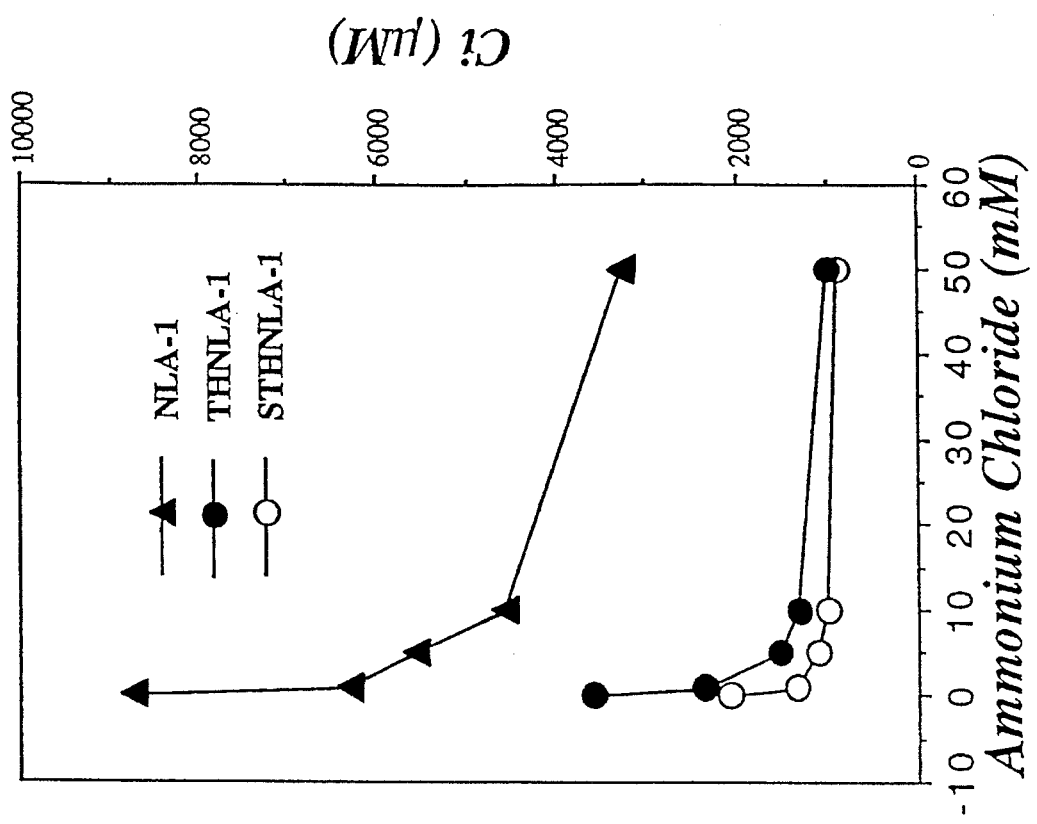
FIG. 10A is a plot of $C_e$ and $C_i$ (μM) of S-THNLA-1 (measured at 330nm) vs. $NH_4Cl$ concentration.
FIG. 10B is a plot of $C_i$ (measured at 330nm) vs. $NH_4Cl$ concentration comparing the effect of $NH_4Cl$ on intracellular accumulation of THNLA-1, S-THNLA-1 and NLA-1 in aerobic V79 cells.
Figure 10:
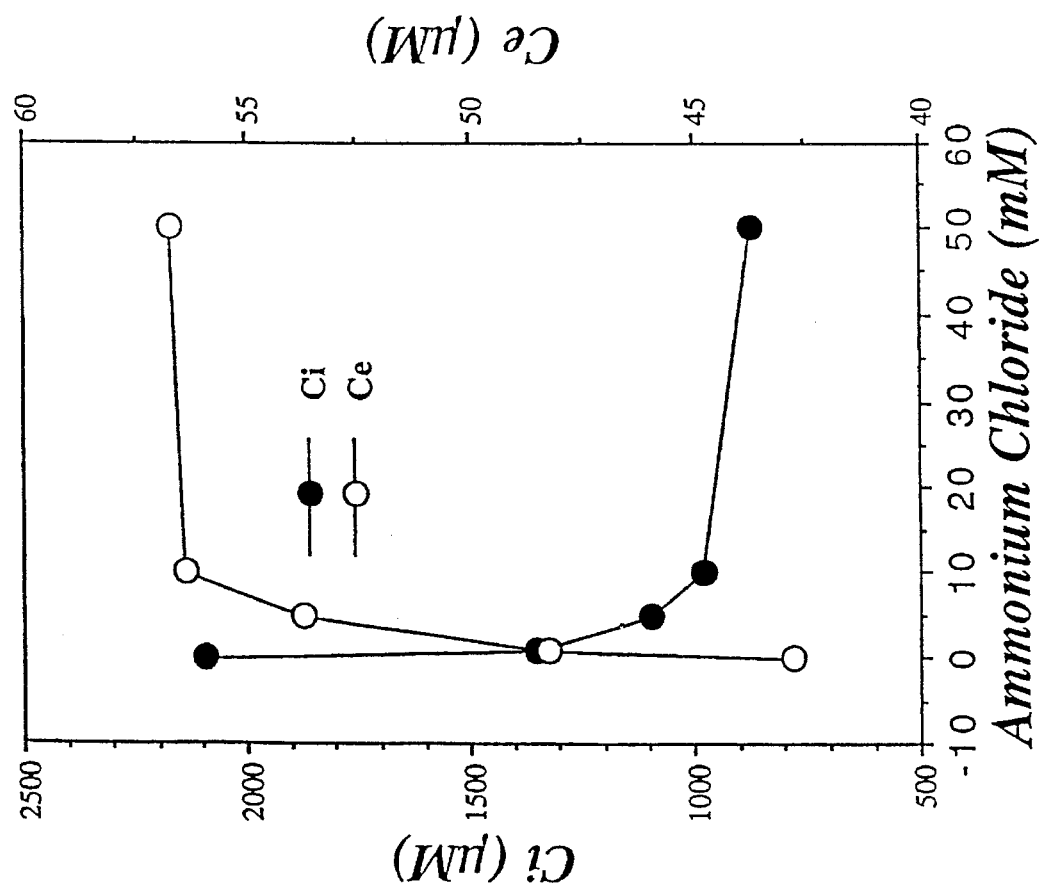

FIGS. 2, 4, 6, 8 and 10 illustrate that S-THNLA-1, Me-THNLA-1 and NLCPQ-1 possess properties similar to THNLA-1 with respect to concentration dependent cytotoxicity (FIG. 2), SER (FIG. 4), IsD (FIG. 6), V79 cell uptake (FIG. 8) and effect of ammonium chloride (FIG. 10).

TABLE I

A Comparison of Physicochemical Properties, Biological Activities and Drug Uptake in V79 Cells (37° C.) between THNLA-1 and NLA-1

| Property | THNLA-1 | NLA-1 |
|---|---|---|
| Partition Coefficient in octanol/water:$PC_{o/w}$ | 0.14 | 0.07 |
| Aerobic Cytotoxicity:$IC_{50/A,1h}$ | 360[a] | 84 |
| Hypoxic cytotoxicity:$IC_{50/H,1h}$ | 33 | 15 |
| Hypoxic selectivity:$IC_{50/A,1h}/IC_{50/H,1h}$ | 11 | 5.5 |
| Hypoxic radiosensitizing potency:$C_{1.6}$ | 19 | 8 |
| Intracellular concentration at $C_{1.6}$:$C_{1.6i}$ | 443 | 885 |
| Therapeutic index (ThI):$IC_{50/A,1h}/C_{1.6}$ | 20–30 | 11 |
| Isoeffective to the oxygen dose at 7.5 Gy:$IsD_{(7.5)}$ | 40 | 11 |
| Topo I inhibition (50%)-dose: | about 600 | about 12 |

[a] All concentrations are in μM.

TABLE II

Physicochemical Properties, Biological Activities and Drug Uptake in V79 Cells (37° C.) for S-THNLA-1, MeN-THNLA-1 and NLCPQ-1

| Property | S-THNLA-1 | MeN-THNLA-1 | NLCPQ-1 |
|---|---|---|---|
| Partition Coefficient in octanol/water: $PC_{o/w}$ | 0.40 | 0.41 | 0.30 |
| Aerobic Cytotoxicity:$IC_{50/A,1h}$ | 580[a] | 426 | 170 |
| Hypoxic cytotoxicity:$IC_{50/H,1h}$ | 68 | 196 | 22 |
| Hypoxic selectivity:$IC_{50/A,1h}/IC_{50/H,1h}$ | about 9 | about 2.2 | about 8 |
| Hypoxic radiosensitizing potency:$C_{1.6}$ | 40 | 59 | 7 |
| Intracellular concentration at $C_{1.6}$:$C_{1.6i}$ | 932 | 586 | 209 |
| Therapeutic index (ThI):$IC_{50/A,1h}/C_{1.6}$ | about 15 | about 7 | about 25 |
| Isoeffective to the oxygen dose at 7.5 Gy:$IsD_{(7.5)}$ | 60 | nd | 25.5 |
| Topo I inhibition (50%)-dose: | about 800 | nd | nd[b] |

[a] All concentrations are in μM.
[b] Not determined.

As previously stated, hypoxic tissues are resistant to radiation therapy and chemotherapeutic drugs. The resistance to chemotherapy is attributed to the distance of the target from viable blood vessels, a slower rate of proliferation, and to the hypoxic environment itself. In addition Lo sensitizing hypoxic cells to radiation treatment, the bioreductive drugs of the present invention also have shown a therapeutic gain when combined with chemotherapeutic alkylating agents. It has been hypothesized, but not relied upon herein, that the therapeutic gain is a result of potentiating alkylating agent-induced DNA crosslinks by metabolites of nitroimidazole.

To demonstrate the usefulness of the compounds of structural formula (I), chemosensitization studies were performed with THNLA-1 using melphalan (i.e., L-PAM) or cis-DDP as the chemotherapeutic agents. L-PAM, also known as phenylalanine mustard and available from Sigma Chem. Co., St. Louis, Mo., first was dissolved in an ethanolic solution of HCl (0.5N). The ethanolic HCl solution was buffered with propylene glycol in a 1:9 ratio of ethanolic HCl solution to propylene glycol, and finally diluted 100 fold with suspension medium. cis-DDP, a platinum-based chemotherapeutic agent available from Sigma Chem. Co., St. Louis, Mo., was dissolved in water to a predetermined concentration.

To examine the "preincubation effect" of the compounds of general formula (I), V79 cells were exposed to a fixed concentration of THNLA-1 for 2 hours under hypoxic conditions, followed by exposure to varying concentrations of L-PAM or cis-DDP for 1 hour under aerobic conditions at 37° C., and then assayed for colony formation. In evaluating the effect of "preincubation time" on chemosensitization, V79 cells were exposed to fixed concentrations of THNLA-1 under conditions of hypoxia for 0 to 4 hours at 37° C., followed by exposure to L-PAM (2 µg/ml) or cis-DDP (30 µM) under aerobic conditions for 1 hour at 37° C., and then assayed for colony formation. THNLA-1 dose-dependent potentiation also was examined by exposing V79 cells to various THNLA-1 concentrations for 2 hours at 37° C. under hypoxic conditions, and then to a fixed dose of each chemotherapeutic agent for 1 hour at 37° C. under aerobic conditions. Experiments using a simultaneous addition of the sensitizer and chemotherapeutic agent for 1 hour at 37° C. under aerobic conditions were also performed.

In all experiments, controls for the hypoxic cytotoxicity of the sensitizer and the toxicity of the chemotherapeutic alone were included. Survival curves were normalized for the hypoxic cytotoxicity of sensitizer in order to determine the dose modification factor (DMF), i.e., the ratio of chemotherapeutic agent concentrations required to reduce cell survival to a predetermined level (e.g., 0.5) alone or in combination with a sensitizer. Synergism between the chemotherapeutic agent and the chemosensitizer was determined using the fractional product concept which is applied in instances of independent action of drugs, or by isobologramic analysis. The results of the chemosensitization studies are illustrated in FIGS. 12–15.

Figure 14:
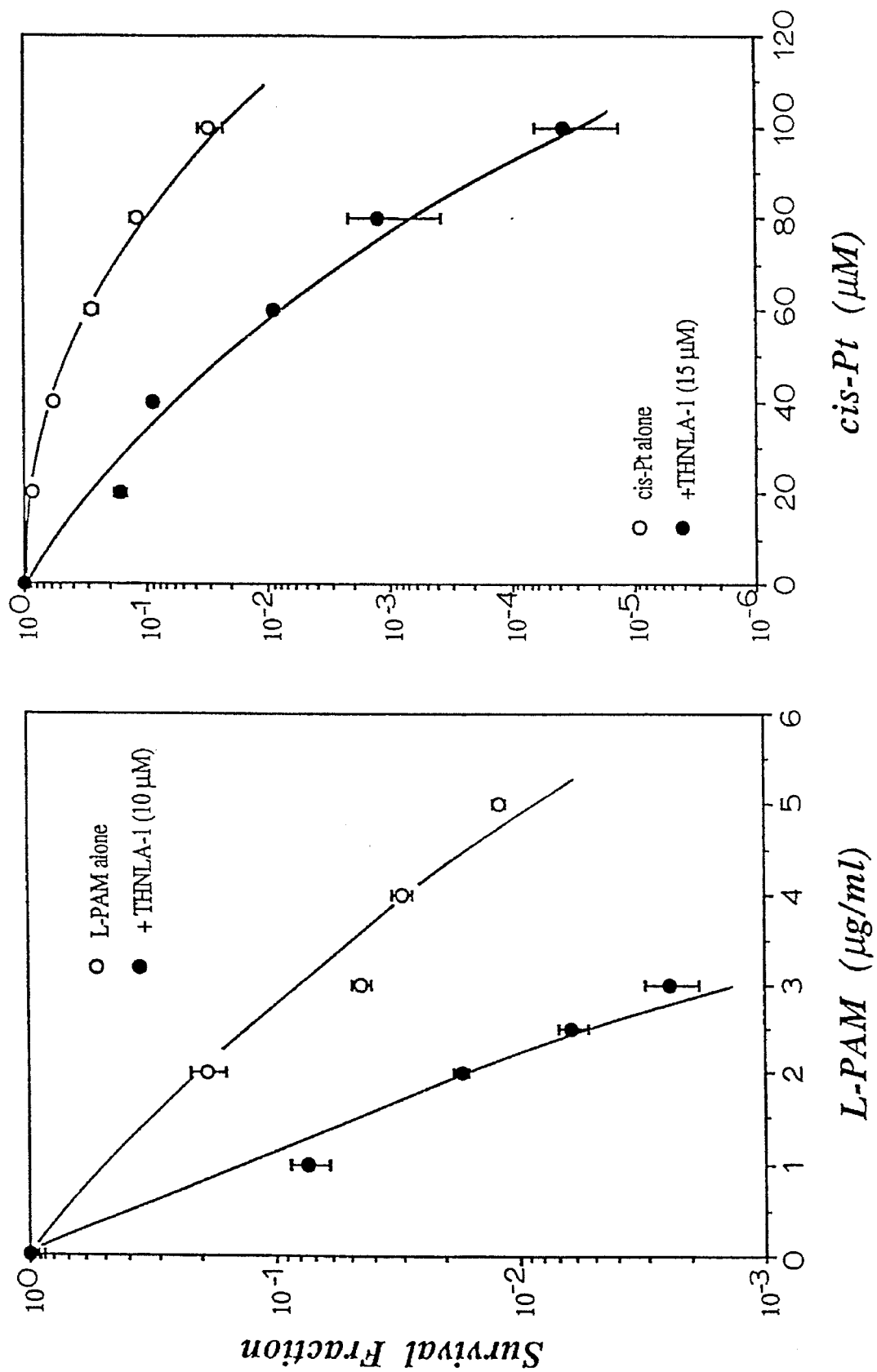
FIGS. 14A and 14B are plots of survival fraction of V79 cells vs. L-PAM (μg/ml) or cis-DDP (μM) concentration, wherein L-PAM or cis-DDP is present alone or in combination with THNLA-1.

With further respect to chemosensitization, isobologramic analysis and analysis according to the fractional product concept clearly demonstrated a synergistic interaction between THNLA-1 and each chemotherapeutic agent (e.g., L-PAM and cis-DDP) under hypoxic pretreatment conditioning of the V79 cells. The synergistic effect is related to the hypoxia pretreatment time with THNLA-1 (FIG. 12), on THNLA-1 concentration (FIG. 13), and the concentration of the chemotherapeutic drug (FIG. 14). The DMF values of L-PAM and cis-DDP at 0.5 survival fraction are 3.2 and 4.2, respectively, when 10 or 15 µM of THNLA-1 was used, respectively. Isobolograms for a survival fraction of 0.316 are shown in FIG. 15.

Figure 12B:
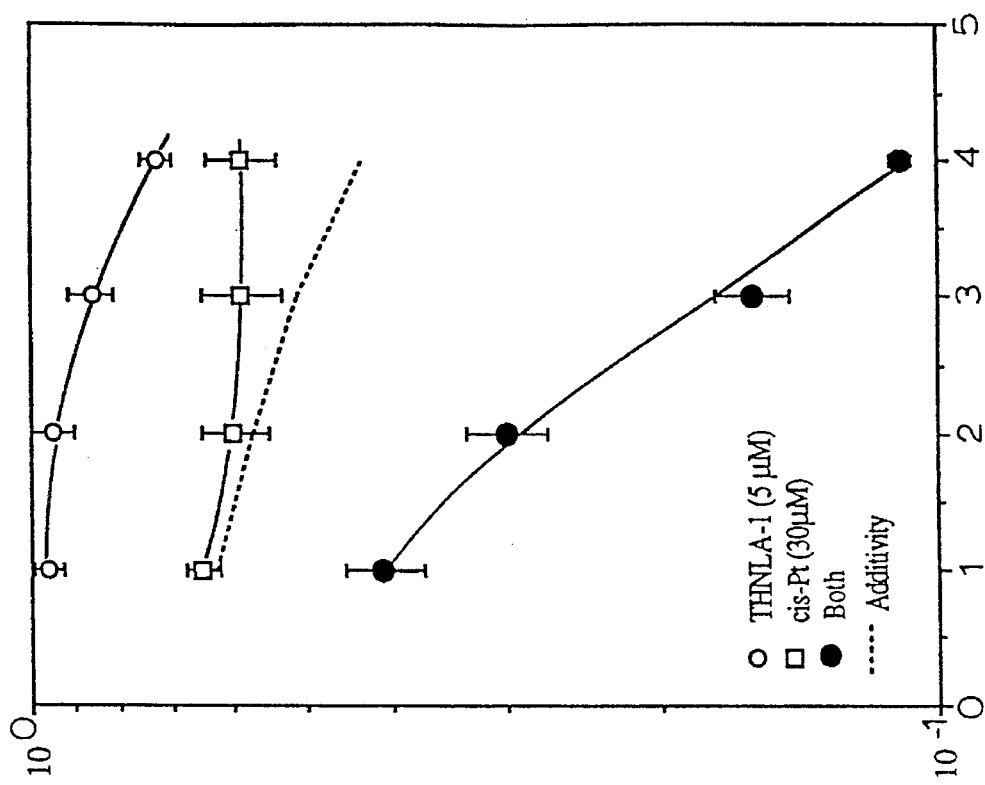
FIGS. 12A and 12B are plots of survival fraction of V79 cells vs. hypoxia treatment time in the presence of THNLA-1, L-PAM or cis-DDP, a combination of THNLA-1 and L-PAM or cis-DDP, and the survival fraction expected from a combination of THNLA-1 and L-PAM or cis-DDP.
Figure 12A:
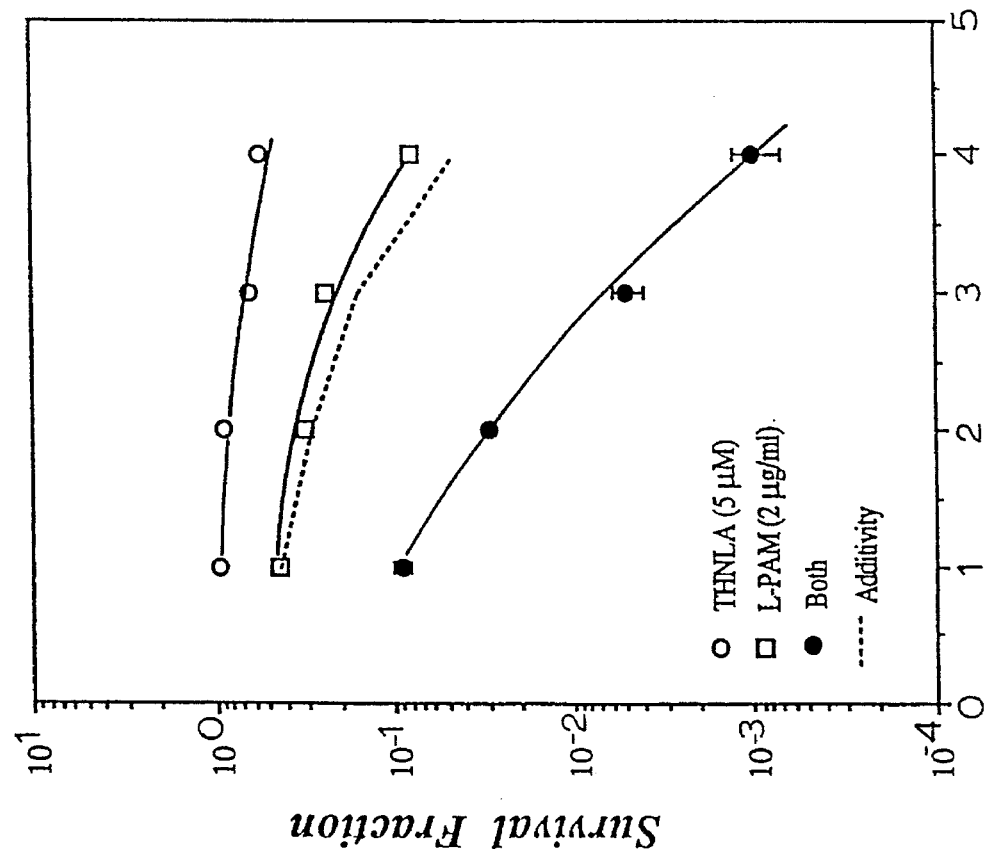

With further respect to FIGS. 12 and 13, the dashed lines represent the expected additive effect of combining THNLA-1 with either L-PAM or cis-DDP. In FIG. 12, the V79 cell samples were exposed to THNLA-1 (5 =M) under hypoxic conditions for a time period of one to four hours prior to a one hour aerobic exposure to either L-PAM or cis-DDP. In FIG. 13, the V79 cell samples were exposed to a THNLA-1 concentration of 0 to 40 mM for 2 hours under hypoxic conditions prior to one hour aerobic exposure to L-PAM Dr cis-DDP. The survival fraction was observed, and illustrated the synergistic effect of combining THNLA-1 with each chemotherapeutic compound tested.

FIG. 14 illustrates a dramatic decrease in survival fraction when a fixed amount THNLA-1 is combined with L-PAM or cis-DDP over a wide concentration range. The V79 cells were exposed to 10 or 15 µM of THNLA-1 for two hours under hypoxic conditions prior to aerobic exposure to L-PAM or cis-DDP for one hour, respectively.

Figure 15:
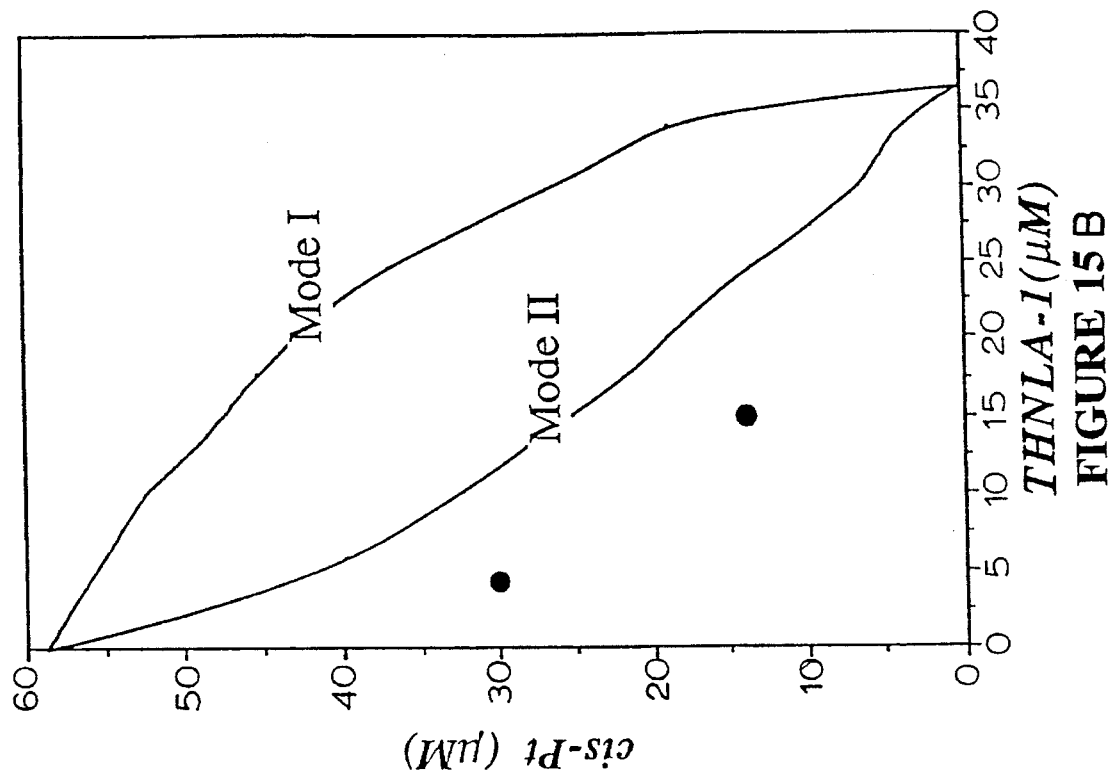
FIGS. 15A and 15B are isobolograms plotting THNLA-1 concentration vs. L-PAM (μM) or cis-DDP (μM) concentrations showing the zones of synergistic, additive and antagonistic effects, and that experimental data of the combination treatment with THNLA-1 and L-PAM or cis-DDP falls within the synergistic zone.
Figure 15:
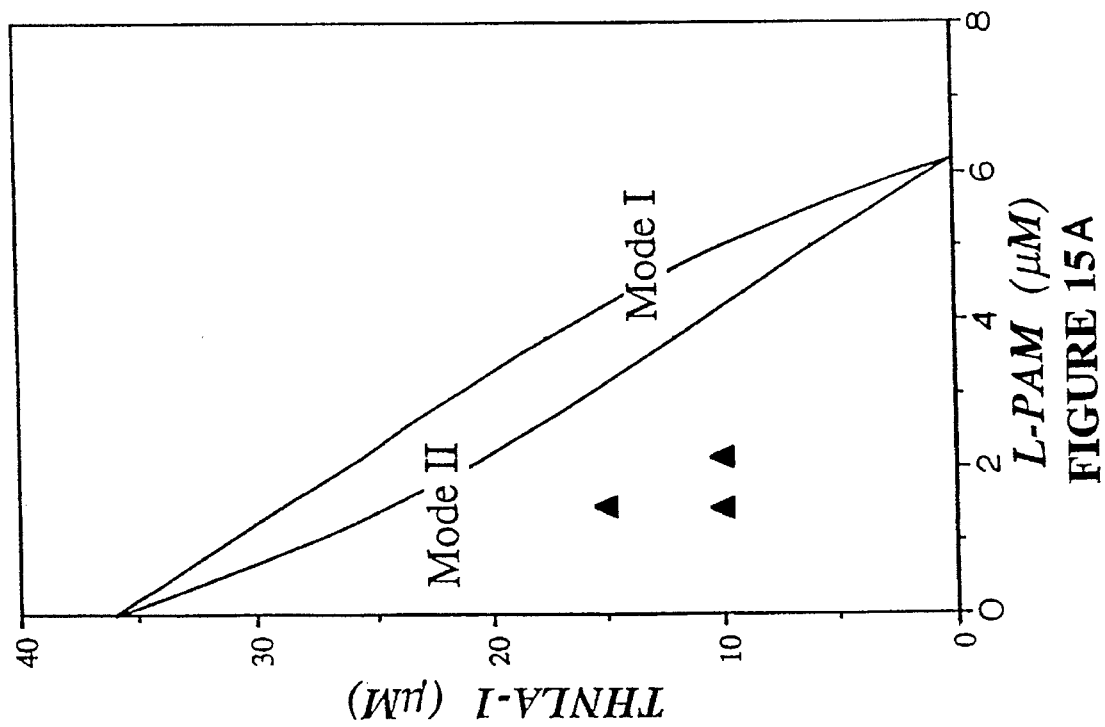

The isobolograms of FIG. 15 clearly show the synergistic effect of combining THNLA-1 with L-PAM or cis-DDP. If the effect of combining THNLA-1 with L-PAM or cis-DDP was purely additive, tile plotted points would fall in the zone within the curves labeled Mode I and Mode II, i.e., the envelope of additivity. If the combination of THNLA-1 and L-PAM or cis-DDP is antagonistic, the plotted points would fall in the zone to the right of the envelope of additivity. In an isobologram, like FIG. 15, a combination is synergistic when the plotted points fall to the left of the envelope of additivity. Accordingly, the combination of THNLA-1 and L-PAM or cis-DDP exhibits an unexpected synergistic effect. The plotted points in FIG. 15 represent a treatment using THNLA-1 and L-PAM or cis-DDP producing a survival fraction of 0,316.

THNLA-1 therefore is a powerful potentiator of chemotherapeutic agent toxicity against V79 cells. Isobologramic and fractional product concept analysis showed that synergistic interaction occurs between THNLA-1 and the chemotherapeutic agents L-PAM and cis-DDP under hypoxic pretreatment conditions. The magnitude of the synergistic effect is related to hypoxia pretreatment time with THNLA-1, to THNLA-1 concentration, and to the concentration of the chemotherapeutic drug. A longer hypoxic preexposure time and a lower sensitizer dose are preferred over a shorter hypoxic preexposure time and a higher sensitizer dose. Other experiments showed that THNLA-1 also effectively chemosensitizes OVCAR cells to L-PAM and cis-DDP. OVCAR cells are resistant to L-PAM and cis-DDP.

Tests also were performed using S-THNLA-1 or NLCPQ-1 with L-PAM or cis-DDP. Those tests showed that S-THNLA-1 and NLCPQ-1, like THNLA-1, are strong chemosensitizers of V-79 cells to L-PAM and cis-DDP.

In accordance with an important feature of the present invention, the usefulness of the hypoxia selective cytotoxins having structural formula (I) as radiation therapy and chemotherapy sensitizers has been demonstrated. Although THNLA-1 is about a two times less potent cytotoxin of hypoxic cells than the prior art NLA-1 compound (i.e., $IC_{50/H,1h}$:33 versus 15 µM), THNLA-1 is about four times less cytotoxic under aerobic conditions ($IC_{50/A,1h}$:360 versus 82 µM) and, therefore, is about two times more selective towards hypoxic V79 cells than NLA-1 (11 versus 5.5). This improved hypoxia selectivity has been attributed to a decrease in aerobic toxicity mediated by mechanisms independent of bioreduction. The decreased toxicity of THNLA-1 under hypoxic conditions compared to NLA-1 can be a result of differences in bioreduction rates in combination with differences in uptake factors.

THNLA-1 also has a superior therapeutic index (ThI) compared to NLA-1. As a radiosensitizer of hypoxic cells, THNLA-1 is about two times more potent than NLA-1 on the basis of the $C_{1.6i}$ values ($C_{1.6i}$:0.443 versus 0.885 mM, respectively), even though comparison of only $C_{1.6}$ values lead to opposite conclusions ($C_{1.6}$:19 versus 8 µM, respectively). Similar behavior has been observed in the case of 5-nitroquine (5-NQ) and 1-nitracrine (1-NC), two prior art compounds that are structurally related to THNLA-1 and NLA-1, respectively. Also, based on the $C_{1.6i}$ values, THNLA-1 is a more potent radiosensitizer of hypoxic cells than misonidazole and the weak base pimonidazole (0.70 and 0.69 mM, respectively). A maximum SER value of 3.1 was achieved with THNLA-1 (e.g., 100 μM, 28% of $IC_{50/A,1h}$) because of the low toxicity of THNLA-1.

The in vitro therapeutic indices (ThI) for S-THNLA-1 and MeN-THNLA-1 are not significantly different from the therapeutic index of the prior art NLA-1 (about 15 and about 7, respectively, versus 11). S-THNLA-1, which is more hypoxia selective, also has a better therapeutic index than NLA-1. S-THNLA-1 is a better hypoxia selective cytotoxin than the fully aromatic NLA-1 (having a differential toxicity of about 9 versus 5.5, respectively). MeN-THNLA-1 has a differential toxicity of 2.2, indicating that for MeN-THNLA-1 the binding affinity to DNA is not correlated to differential toxicity.

NLCPQ-1, S-THNLA-1 and MeN-THNLA-1 also are very efficient radiosensitizers with maximum SER values (equal to OER) at non-toxic concentrations. However, on a concentration basis S-THNLA-1 and MeN-THNLA-1 appear less potent than NLA-1 and THNLA-1, which is attributed to a different uptake by V79 cells. However, based on $C_{1.6i}$ values, MeN-THNLA-1 is a more potent radiosensitizer than NLA-1, miso and pimonidazole.

NLCPQ-1, on the other hand, has a potency as a radiosensitizer that is similar to NLA-1 ($C_{1.6}$ of 7 for NLCPQ-1, $C_{1.6}$ of 8 for NLA-1). The ThI of NLCPQ-1 is 25, which is superior to the THI of 11 exhibited by NLA-1. Based again on the $C_{1.6i}$ values on Table II, NLCPQ-1 is 4.2 times more potent than NLA-1, and is the most potent of all the tested compounds as a radio- or chemosensitizer and as a hypoxia selective cytotoxin.

No radiosensitization was observed under hypoxic conditions when THNLA-1 was given immediately after radiation. Therefore, a hypoxia selective cytotoxin of the present invention should be present at the target site at time of irradiation. In addition, it was observed that no radioprotection occurred under aerobic conditions. The prior art NLA-1 compound has afforded radioprotection under aerobic conditions. The aerobic radioprotection provided by NLA-1 helps explain the failure of NLA-1 as radiosensitizer in solid tumors where not all regions of the tumor are hypoxic. Aerobic radioprotection also has been observed with phenanthridium compounds. In accordance with another important feature of the present invention, the ability to radiosensitize under hypoxic conditions, and not to radioprotect under aerobic conditions, illustrates an important potential clinical advantage of the hypoxia selective cytotoxins having general structural formula With respect to chemosensitization, the DMF values obtained for a combination of cis-DDP or L-PAM with THNLA-1 were slightly greater than the DMF value obtained using a combination including NLA-1 (using about 30% of the $IC_{50/H,1h}$). However, based on the intracellular concentration level ($C_i$) of the two compounds, THNLA-1 is a significantly more efficacious chemosensitizer than NLA-1. The fact that no potentiation occurred when cells were exposed to THNLA-1 and L-PAM or cis-DDP under aerobic conditions is further indicative that no systemic toxicity due to THNLA-1 should be expected in vivo.

The relatively high THNLA-1 concentrations required for Topo-I inhibition (600 μM versus 12 μM for NLA-1) helps explain the unexpectedly low aerobic toxicity of THNLA-1. Furthermore, inhibition of the catalytic activity of Topo-I without induction of Topo I-dependent single-stranded DNA cleavage is not lethal to the cell. Such cleavage is not observed with THNLA-1, while it has been observed with NLA-1.

In conclusion, the DNA-affinic compounds of the present invention are an improvement over the prior acridine-based NLA compounds as hypoxia selective cytotoxins, radiosensitizers and chemosensitizes. For example, THNLA-1 has a two-to-three times greater in vitro therapeutic index than NLA-1. In vivo tests using THNLA-1, S-THNLA-1, MeN-THNLA-1 and NLCPQ-1 are designed to illustrate the usefulness of the new and improved bioreductive drugs in potential clinical use.

Figure 16B:
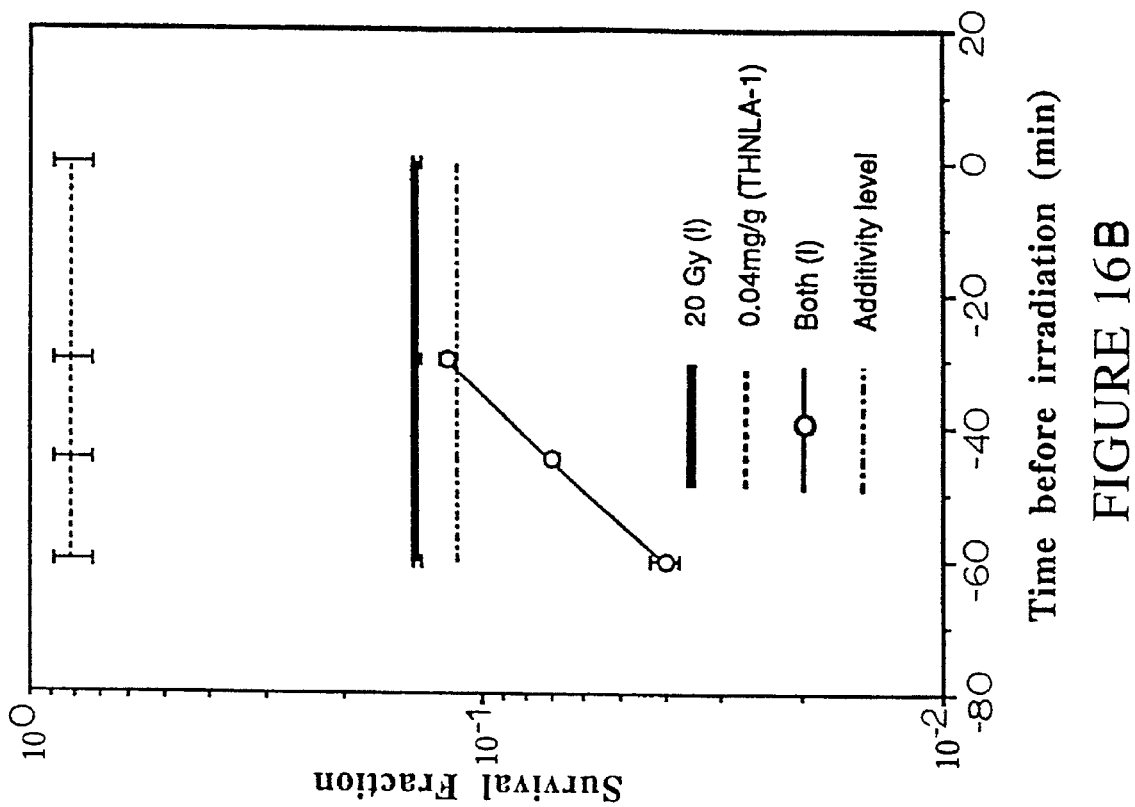
FIGS. 16A and 16B are plots of survival fraction vs. time of THNLA-1 administration (0.103 mmol/g) before irradiation (min) for replicate tests performed on tumor-bearing mice to determine the radiosensitizing effects of THNLA-1 in vivo.
Figure 16A:
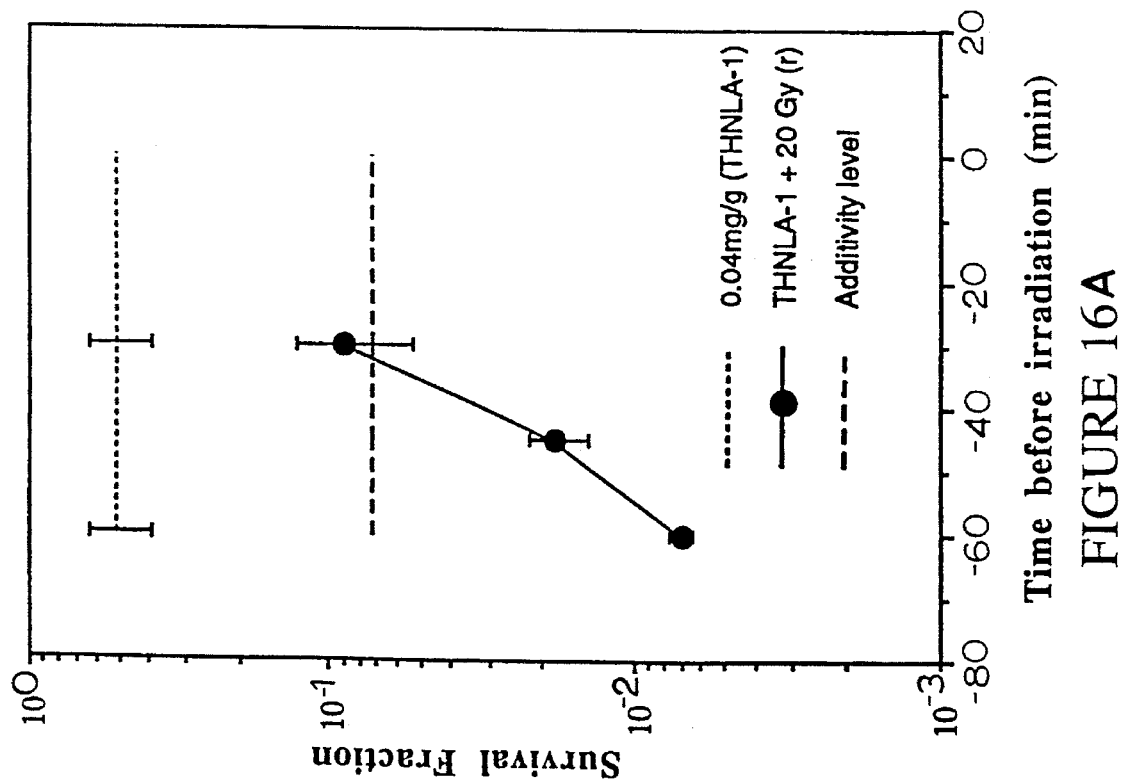

FIGS. 16 and 17 illustrate in vivo radiosensitization tests using THNLA-1 (FIG. 16) or etanidazole (FIG. 17), a prior sensitizer, either alone or in combination with a single radiation dose (20 Gy). FIGS. 16A and 16B illustrate replicate sets of experiments wherein THNLA-1 was administered to balb mice bearing two EMT6 tumors. The THNLA-1 was administered at a concentration of 0.103 mmol/g, intraperitoneally, either 60, 45 ,or 30 minutes prior to irradiation at 20 Gy. EMT6 tumor:s exhibit up to 20% hypoxia.

FIGS. 16A and 16B also show the toxicity of THNLA-1 alone (short-dashed line). FIG. 16B shows the toxicity of radiation (20 Gy) alone (solid line). FIGS. 16A and 16B also illustrate the expected additive effect of radiation and THNLA-1 (long-dashed line and dot-dash line in FIGS. 16A and 16B, respectively), and illustrate the synergistic effect of combining radiation with a pretreatment of THNLA-1.

A toxicity study performed on balb mice showed that THNLA-1 is nontoxic at a concentration of at least 0.129 mmol/g. Therefore the dose of 0.103 mmol/g used in the experiment illustrated in FIG. 16 can be increased for optimum sensitivity. THNLA-1 also exhibits a potent radiosensitizing effect at 0.103 mmol/g in vivo. Finally, the degree of radiosensitivity is related to the amount of time lapsing between THNLA-1 administration and subsequent radiation. FIGS. 16A and 16B particularly show that radiosensitization is maximized when the THNLA-1 is administered at least one hour before irradiation.

Figures 17A, 17B:
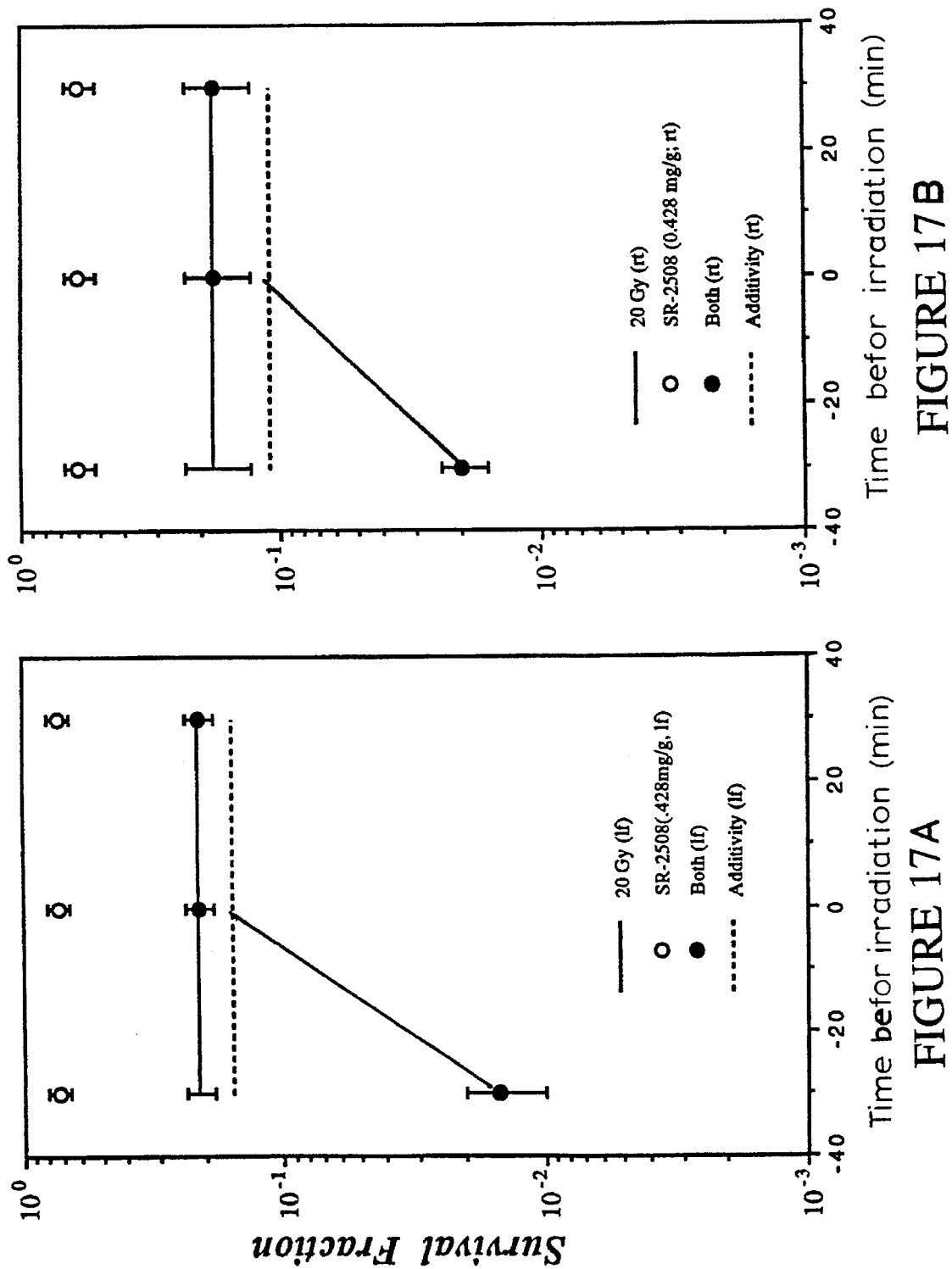
FIGS. 17A–C are plots of survival fraction vs. time of etanidazole administration (2 mmol/g) before irradiation (min) for replicate tests performed on tumor-bearing mice to determine the radiosensitizing effects of etanidazole in vivo.
Figure 17C:
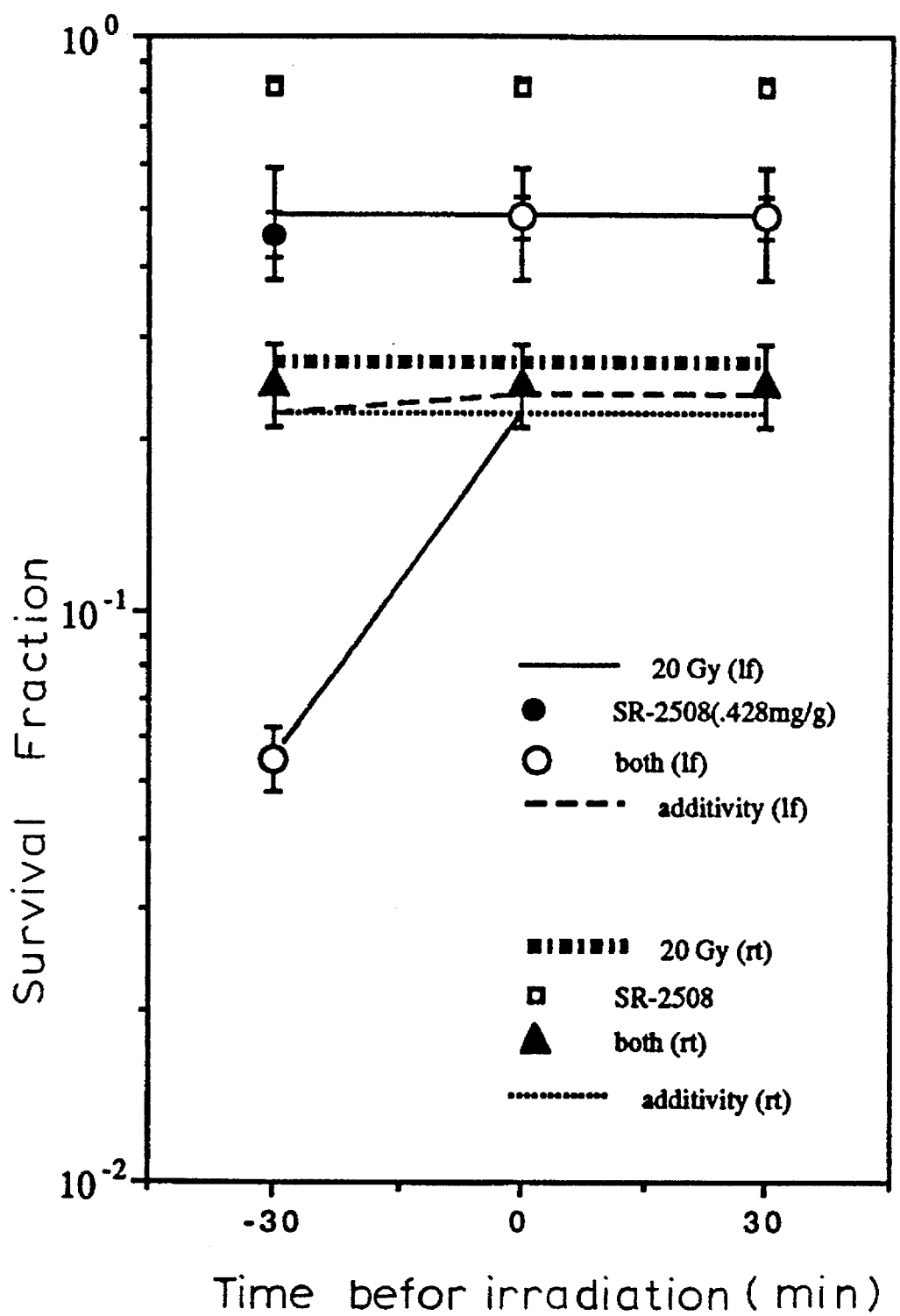

FIGS. 17A–C illustrate experiments similar to those illustrated in FIGS. 16A–B, except the radiosensitizer was the prior art compound, etanidazole (i.e., SR-2508), administered at 2 mmol/g. A comparison between FIG. 16 and FIG. 17 shows that THNLA-1, at 0.103 mmol/g, enhanced the effects of 20 Gy radiation in EMT6 tumors to a similar degree as 2 mmol/g of etanidazole, i.e., THNLA-1 performs essentially equally as a radiosensitizer to etanidazole at about one-twentieth of the dose.

Obviously, many modifications and variations of the invention as hereinbefore set forth can be made without departing from the spirit and scope thereof and therefore only such limitations should be imposed as are indicated by the appended claims.

We claim:

1. A hypoxia selective cytotoxin having the structural formula:

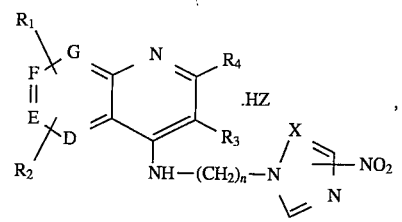

wherein

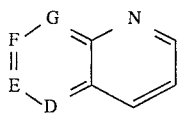

is selected from the group consisting of

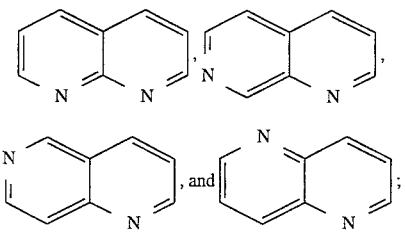

$R_1$ and $R_2$, independently, are selected from the group consisting of methyl, halo, hydrogen, trifluoromethyl, methoxy, cyano, and methylsulfo; $R_3$ and $R_4$ taken together are a five or six-membered nonaromatic ring system; n is an integer 1 through 5; X is carbon or nitrogen; and Z is a physiologically acceptable anion.

2. The cytotoxin of claim 1 wherein $R_3$ and $R_4$ are taken together to form a five or six-membered nonaromatic carbocyclic ring.

3. The cytotoxin of claim 1 wherein $R_3$ and $R_4$ are taken together to form a five or six-membered nonaromatic ring incorporating an oxygen atom, a sulfur atom or a nitrogen atom.

4. The cytotoxin of claim 1 wherein $R_3$ and $R_4$, when taken together to form a five or six-membered non-aromatic ring, is selected from the group consisting of —(CH$_2$)$_3$—, —CHMe(CH$_2$)$_2$—, —CH$_2$CHMeCH$_2$—, —(CH$_2$)$_2$CHMe—, —(CH$_2$)$_4$—, —CHMe(CH$_2$)$_3$—, —CH$_2$CHMe(CH$_2$)$_2$—, —(CH$_2$)$_2$CHMeCH$_2$—, —(CH$_2$)$_3$CHMe—, —SCH$_2$CH$_2$—, —CH$_2$SCH$_2$—, —CH$_2$SCH$_2$CH$_2$—, —CH$_2$OCH$_2$—, —CH$_2$OCH$_2$CH$_2$—, —CH$_2$NR$_5$CH$_2$CH$_2$—, —(CH$_2$)$_3$NR$_5$— and —(CH$_2$)$_2$NR$_5$—, wherein Me is methyl and $R_5$ is methyl or ethyl.

5. The cytotoxin of claim 1 wherein n is an integer two through four.

6. The cytotoxin of claim 1 wherein

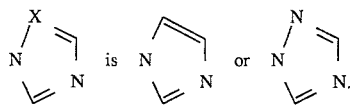

7. The cytotoxin of claim 1 wherein HZ is selected from the group consisting of hydrochloric acid, phosphoric acid, nitric acid, perchloric acid, tetrafluoroboric acid, sulfuric acid, and mixtures thereof.

8. A method of chemosensitization comprising administering an effective amount of the hypoxia selective cytotoxin of claim 1 to a tumor or tumor cells, then administering a chemotherapeutic agent.

9. The method of claim 8 wherein the chemotherapeutic agent is selected from the group consisting of L-PAM, cis-DDP, cyclophosphamide, a nitrosourea, and doxorubicin.

10. A hypoxia selective cytotoxin having the structural formula:

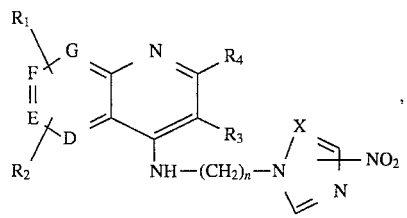

wherein

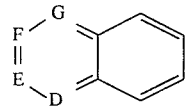

is selected from the group consisting of

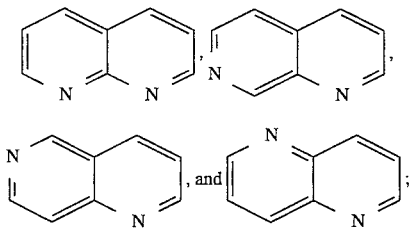

$R_1$ and $R_2$, independently, are selected from the group consisting of methyl, halo, hydrogen, trifluoromethyl, methoxy, cyano, and methylsulfo; $R_3$ and $R_4$ taken together are a five or six-membered nonaromatic ring system; and n is an integer 1 through 5; X is carbon or nitrogen.

11. A hypoxia selective cytotoxin having the structural formula:

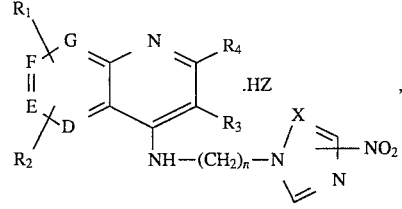

wherein D, E, F, and G, independently, are carbon or nitrogen, with the proviso that three or more of D, E, F, and G are carbon; $R_1$ is methyl; $R_2$ is methyl; $R_3$ and $R_4$ taken together are a five- or six-membered nonaromatic ring system; n is an integer 1 through 5; X is carbon or nitrogen, and Z is a physiologically acceptable anion.

12. A hypoxia selective cytotoxin having the structural formula:

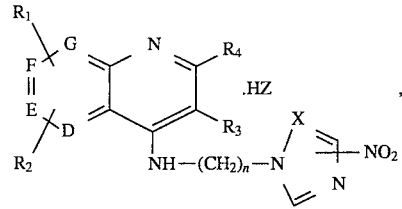

wherein D, E, F, and G, independently, are carbon or nitrogen, with the proviso that three or more of D, E, F, and G are carbon; $R_1$ is fluoro; $R_2$ is fluoro; $R_3$ and $R_4$ taken together are a five- or six-membered nonaromatic ring system; n is an integer 1 through 5; X is carbon or nitrogen, and Z is a physiologically acceptable anion.

13. A hypoxia selective cytotoxin having the structural formula:

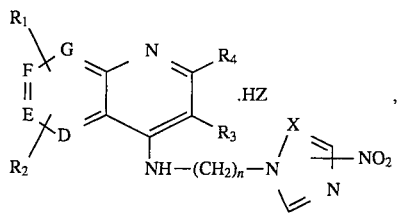

wherein D, E, F, and G, independently, are carbon or nitrogen, with the proviso that three or more of D, E, F, and G are carbon; $R_1$ is methoxy; $R_2$ is methoxy; $R_3$ and $R_4$ taken together are a five- or six-membered nonaromatic ring system; n is an integer 1 through 5; X is carbon or nitrogen, and Z is a physiologically acceptable anion.

14. A hypoxia selective cytotoxin having the structural formula:

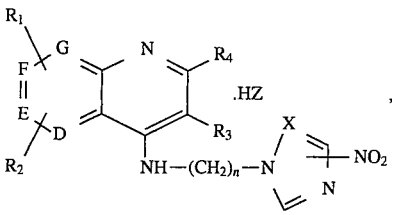

wherein D, E, F, and G, independently, are carbon or nitrogen, with the proviso that three or more of D, E, F, and G are carbon; $R_1$ is chloro; $R_2$ is chloro; $R_3$ and $R_4$ taken together are a five- or six-membered nonaromatic ring system; n is an integer 1 through 5; X is carbon or nitrogen, and Z is a physiologically acceptable anion.

15. A hypoxia selective cytotoxin selected from the group consisting of 9-[3-(2-nitro-1-imidazolyl)propylamino]-cyclopenten[b]quinoline hydrochloride, having the structure:

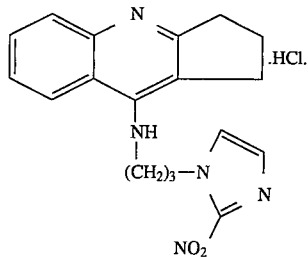

16. A method of chemosensitization comprising administering an effective amount of a hypoxia selective cytotoxin to a tumor or tumor cells, said hypoxia selective cytotoxin selected from the group consisting of 9-[3-(2-nitro-1-imidazolyl)propylamino]cyclopenten[b]quinoline hydrochloride, having the structure:

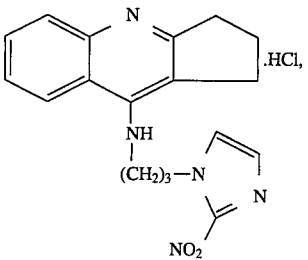

then administering a chemotherapeutic agent.

* * * * *

UNITED STATES PATENT AND TRADEMARK OFFICE
CERTIFICATE OF CORRECTION

PATENT NO.    :   5,602,142
DATED         :   February 11, 1997
INVENTOR(S)   :   Papadopoulou-Rosenzweig et al.

It is certified that error appears in the above-identified patent and that said Letters Patent is hereby corrected as shown below:

Column 2, line 45, between "aerobic" and "and" insert --cells--

Column 10, between lines 25-30, under the first chemical structure, "(II)" should be --(III)--

Column 12, line 20, the sentence beginning "The five-membered" should be a new paragraph Column 12, line 57, "radio-or" should be -- radio- or --

Column 15, line 30, "S-THLA-1" should be -- S-THNLA-1 --

Column 16, line 60, "POC$_3$" should be --POCl$_3$--

Column 17, line 2, "ethanol: ethyl" should be --ethanol:ethyl--

Column 17, lines 23, 24, "3(2-nitro-1-imidazolyl)propylamine" should be -- 3-(2-nitro-1-imidazolyl)propylamine --

Column 17, line 39, "MH+:m/z" should be --MH$^+$:m/z--

Column 19, lines 21, 22, "clonogenicity) under hypoxia (H) or air (A) was" should be moved to column 19, line 20, between "of" and "determined"

Column 19, line 33, "NLCPQ I" should be -- NLCPQ-1 --

Column 19, line 35, "MeN-THNLA I" should be -- MeN-THNLA-1 --

UNITED STATES PATENT AND TRADEMARK OFFICE
CERTIFICATE OF CORRECTION

PATENT NO.   :   5,602,142
DATED        :   February 11, 1997
INVENTOR(S)  :   Papadopoulou-Rosenzweig et al.

It is certified that error appears in the above-identified patent and that said Letters Patent is hereby corrected as shown below:

Column 22, line 25, "THNLA-3" should be -- THNLA-1 --

Column 22, line 38, "Nacl," should be --NaCl,--

Column 22, line 46, "reaction n mixtures" should be --reaction mixtures--

Column 24, line 56, "Lo" should be --to--

Column 25, line 57, "(5 =M)" should be --(5 µM)--

Column 25, line 63, "Dr" should be --or--

Column 26, line 19, "0,316." should be --0.316.--

Column 27, line 45, after "formula" insert --(I).--

Signed and Sealed this

Twenty-fifth Day of November, 1997

BRUCE LEHMAN

*Attest:*

*Attesting Officer*        *Commissioner of Patents and Trademarks*